US008648177B2

(12) United States Patent
Guo et al.

(10) Patent No.: US 8,648,177 B2
(45) Date of Patent: Feb. 11, 2014

(54) LYOPHILIZATION METHODS, COMPOSITIONS, AND KITS

(75) Inventors: Jianxin Guo, Chesterfield, MO (US); Anthony Klos, Raleigh, NC (US); Deborah Barnette, Cary, NC (US)

(73) Assignee: Grifols Therapeutics Inc., Research Triangle Park, NC (US)

( * ) Notice: Subject to any disclaimer, the term of this patent is extended or adjusted under 35 U.S.C. 154(b) by 0 days.

(21) Appl. No.: 13/510,401

(22) PCT Filed: Nov. 23, 2010

(86) PCT No.: PCT/US2010/057816
§ 371 (c)(1),
(2), (4) Date: Oct. 31, 2012

(87) PCT Pub. No.: WO2011/066291
PCT Pub. Date: Jun. 3, 2011

(65) Prior Publication Data
US 2013/0040890 A1    Feb. 14, 2013

Related U.S. Application Data

(60) Provisional application No. 61/264,014, filed on Nov. 24, 2009.

(51) Int. Cl.
*A61K 35/16* (2006.01)
*C07K 16/06* (2006.01)
*C07K 14/745* (2006.01)

(52) U.S. Cl.
USPC .......................... 530/393; 514/14.7; 426/384

(58) Field of Classification Search
None
See application file for complete search history.

(56) References Cited

U.S. PATENT DOCUMENTS

| | | | |
|---|---|---|---|
| 4,087,415 A * | 5/1978 | Bick et al. | 530/393 |
| 4,337,242 A | 6/1982 | Markus et al. | |
| 4,340,589 A | 7/1982 | Uemura et al. | |
| 4,496,537 A | 1/1985 | Kwan | |
| 4,517,294 A | 5/1985 | Bock et al. | |
| 4,632,981 A | 12/1986 | Bock et al. | |
| 4,711,848 A | 12/1987 | Insley et al. | |
| 4,732,973 A | 3/1988 | Barr et al. | |
| 4,873,316 A | 10/1989 | Meade et al. | |
| 4,931,373 A | 6/1990 | Kawasaki et al. | |
| 5,032,405 A | 7/1991 | Huang et al. | |
| 5,079,336 A | 1/1992 | Rubin et al. | |
| 5,134,119 A | 7/1992 | Lezdey et al. | |
| 5,218,091 A | 6/1993 | Kawasaki et al. | |
| 5,304,638 A | 4/1994 | Marshall et al. | |
| 5,322,775 A | 6/1994 | Clark et al. | |
| 5,420,252 A | 5/1995 | Kato et al. | |
| 5,561,115 A | 10/1996 | Tenold et al. | |
| 5,618,713 A | 4/1997 | Zettlmeissl et al. | |
| 5,700,663 A | 12/1997 | Zettlmeissl et al. | |
| 5,843,705 A | 12/1998 | Ditullio et al. | |
| 6,072,029 A | 6/2000 | Courtney et al. | |
| 6,441,145 B1 | 8/2002 | Ditullio et al. | |
| 6,586,573 B1 | 7/2003 | Besman et al. | |
| 6,878,813 B2 | 4/2005 | Bock et al. | |
| 6,974,792 B2 | 12/2005 | Mattes et al. | |
| 7,019,193 B2 | 3/2006 | Ditullio et al. | |
| 7,087,723 B2 | 8/2006 | Besman et al. | |
| 7,247,707 B2 | 7/2007 | Besman et al. | |
| 2003/0235555 A1 | 12/2003 | Shealey et al. | |
| 2004/0157911 A1 | 8/2004 | Spireas et al. | |
| 2005/0013867 A1 | 1/2005 | Lehrman et al. | |
| 2005/0070477 A1 | 3/2005 | Cochrane | |
| 2005/0226893 A1 | 10/2005 | Juneau et al. | |
| 2006/0024793 A1 | 2/2006 | Yamada et al. | |
| 2007/0237758 A1 | 10/2007 | Barry et al. | |
| 2008/0312136 A1 | 12/2008 | Durrani et al. | |

FOREIGN PATENT DOCUMENTS

| | | |
|---|---|---|
| WO | WO 02-02793 | 1/2002 |
| WO | WO 2005-027821 | 3/2005 |
| WO | WO 2005-048985 | 6/2005 |
| WO | WO 2007-091267 | 8/2007 |
| WO | WO 2008042408 A2 * | 4/2008 |
| WO | WO 2011-066291 | 6/2011 |

OTHER PUBLICATIONS

Bakaltcheva, et al., Freeze-dried whole plasma: Evaluating sucrose, trehalose, sorbitol, mannitol and glycine as stabilizers, Thrombosis Research 120:105-116, 2007.*
Searles, et al., Annealing to Optimize the Primary Drying Rate, Reduce Freezing-Induced Drying Rate Heterogeneity, and Determine Tg in Pharmaceutical Lyophilization, Journal of Pharmaceutical Sciences, 90(7):872-897, 2001.*
Chang, et al., Physical Factors Affecting the Storage Stability of Freeze-Dried Interleukin-1 Receptor Antagonist: Glass Transition and Protein Conformation, Archives of Biochemistry and Biophysics, 331(2):249-258, 1996.*
Passot, et al., Physical characterisation of formulations for the development of two stable freeze-dried proteins during both dried and liquid storage, European Journal of Pharmaceutics and Biopharmaceutics 60:335-348, 2005.*
Merck Manual for Health Care Professionals.*
Chongprasert, Characterization of Frozen Solutions of Glycine, Journal of Pharmaceutical Sciences 90(11): 1720-1728, 2001.*
Carpenter, 1997, Pharmaceutical Research, 14, 969-975.*
Alpha1-Proteinase Inhibitor (Human) Prolastin, Talecris Biotherapeutics, Inc. (2008).
Antithrombin III (Human) Thrombate III, Talecris Biotherapeutics, Inc. (2006).
Arakawa, T., et al., "The Effects of Protein Stabilizers on Aggregation Induced by Multiple-Stresses," *Yakugaku Zasshi* 123(11): 957-961 (2003) (Abstract).

(Continued)

*Primary Examiner* — Satyanarayana R Gudibande
(74) *Attorney, Agent, or Firm* — Womble Carlyle Sandridge & Rice, LLP

(57) ABSTRACT

Method for lyophilization is provided, in particular methods for lyophilization of formulations comprising AT III. Also provided are compositions prepared by therefrom. Also provided are kits comprising the compositions and/or lyophilized products.

18 Claims, 24 Drawing Sheets

(56) References Cited

OTHER PUBLICATIONS

Archibald et al., "High-level expression of biologically active human a1-antitrypsin in the milk of transgenic mice," *PNAS*, 87:5178 (1990).

Coan, M.H., et al., "Preparation and Properties of Alpha,-Proteinase Inhibitor Concentrate from Human Plasma ," *Vox Sang.*, 48:333-342 (1985).

Fan. B., et al., "Heterogeneity of Recombinant Human Antithrombin III Expressed in Baby Hamster Kidney Cells," *JBC*, 268(23):17588-17596 (1993).

Garone, L., et al., "Antithrombin-Heparin Affinity Reduced by Fucosylation of Carbohydrate at Asparagine 155+," *Biochemistry*, 35:8881 (1996).

Gieseler, H., "Product Morphology and Drying Behavior delineated by a new Freeze-Drying Microbalance," *Thesis*, pp. 1-189 (2004).

Gillespie, L.S., et al., "Expression of Biologically Active Antithrombin III by Recombinant Baculovirus in *Spodoptera frugiperda Cella*," *JBC*, 266:3995-4001 (1991).

Jennings, T.A., "Effect of formulation on lyophilization, part 1. Formulation components—their freezing and drying," *IVD Technology*, pp. 1-4 (1997).

Lu, X, and Pikal, M, "Freeze-drying of Mannitol-trehalose-sodium chloride-based formulations: the impact of annealing on dry layer resistance to Mass Transfer and Ckae Structure , Pharmaceutical Developmenet and Technology," 9(1):85-95 (2004).

Wright et al., "High-Level Expression of Active Human Alpha-1-Antitrypsin In the Mik of Transgenic Sheep," *Biotechnology*, 9:830-834 (1991).

* cited by examiner

A

B

A

B

US 8,648,177 B2

LYOPHILIZATION METHODS, COMPOSITIONS, AND KITS

CROSS-REFERENCE TO RELATED APPLICATIONS

The present application is a national phase of International Application PCT/US10/057,816, filed Nov. 23, 2010, which claims the benefit of priority under 35 USC 119 to U.S. Provisional Application No. 61/264,014 filed Nov. 24, 2009, each of which is herein incorporated by reference in its entirety.

FIELD OF THE INVENTION

The present invention relates to methods for lyophilizing compositions, in particular aqueous pharmaceutical formulations comprising at least one active ingredient, and compositions prepared therefrom, in particular to compositions, kits, and methods for lyophilizing antithrombin-III (AT III).

BACKGROUND OF THE INVENTION

Lyophilization is a commonly used method for preparing active ingredients into more solid forms of pharmaceuticals. For example, an active ingredient such as AT III, which is an $alpha_2$-glycoprotein normally present in plasma and is a plasma inhibitor of thrombin, has been shown to have relatively poor stability in solution. Accordingly, AT III has been processed into lyophilized preparations.

It has been proposed that lyophilization reduces or inhibits the degradation of the active ingredient by removing solvent components in a formulation to levels that no longer support chemical reactions or biological growth. Additionally, it is believed that the removal of solvent reduces molecular mobility, reducing potential for degradative reaction. Also, it is desirable for crystallizing excipients (e.g., amino acids and salts), which are commonly used in lyophilized products, to crystallize as completely as possible during freezing in order to provide a solid matrix to support cake structure. However, a number of previous attempts to lyophilize aqueous pharmaceutical formulations have failed to achieve satisfactory degrees of crystallization. For example, the various freezing and/or annealing steps of a typical lyophilization protocol itself have been shown to be inefficient in promoting crystallization. Moreover, it has been suggested that the presence of certain crystallizing excipients (e.g., alanine and sodium chloride) can inhibit or reduce the crystallization of either excipient thereby also limiting the extent of crystallization.

While several attempts have been made to lyophilize aqueous pharmaceutical formulations, there remains a need for effective lyophilization methods and compositions prepared therefrom.

SUMMARY OF THE INVENTION

In one aspect, the present invention provides a method of lyophilizing a composition comprising at least one active ingredient and at least one crystallizing excipient. The method comprises: exposing the composition to a first temperature for a first period of time sufficient to obtain a first composition having the at least one crystallizing excipient partially or completely crystallized.

In another aspect, the present invention provides a method of lyophilizing a liquid composition comprising plasma-derived AT III, NaCl, and alanine. The method comprises:

(a) exposing the composition to about 54° C. or below such that the temperature of the composition is about 48° C. or below for about 5 hours or more in order to provide a first composition having one or more components therein completely or near completely crystallized; and (b) drying the first composition to obtain a lyophilized cake.

In some aspects, the present invention provides compositions including lyophilized cakes prepared in accordance with the methods disclosed herein.

In other aspects, the present invention provides a kit comprising one or more of the compositions and/or the lyophilized cakes prepared in accordance with the methods disclosed herein.

DETAILED DESCRIPTION OF THE INVENTION

Figure 1:
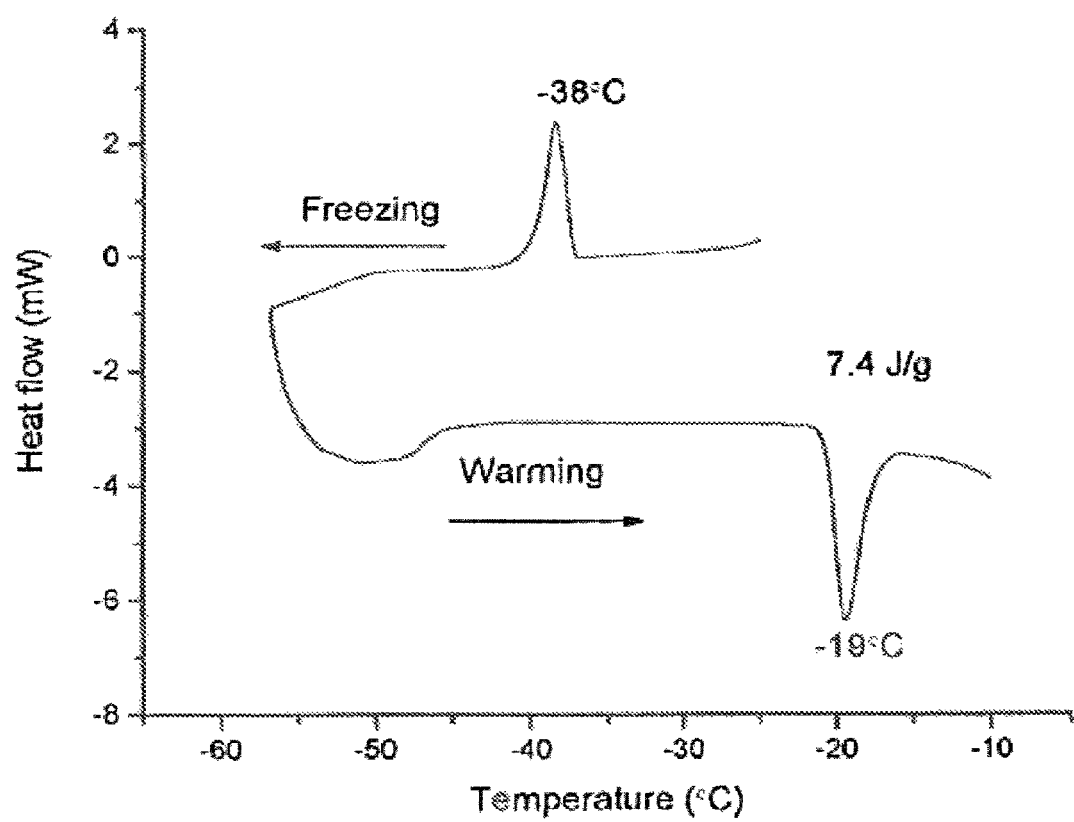
FIG. 1. DSC thermogram during freezing and warming of NaCl solution (0.15M).

The present invention provides the unexpected finding that a single low-temperature freezing step prior to drying is sufficient to induce crystallization of crystallizable excipients in formulations comprising an active ingredient, and thus the present methods provide robust excipient crystallization while also providing a more efficient, practical, and/or robust lyophilization protocol. The present methods allow for an increased degree of crystalline bulking agents over prior methods, while maintaining the stability and activity of the active ingredient present in the formulations.

In one aspect, the present invention provides a method of lyophilizing a composition comprising at least one active ingredient and at least one crystallizing excipient. The method comprises exposing the composition to a first temperature for a first period of time sufficient to obtain a first composition having the at least one crystallizing excipient partially or completely crystallized.

The composition can be a liquid or a semi-liquid composition. For example, the composition can be an aqueous pharmaceutical solution or suspension comprising the at least one active ingredient and the at least one crystallizing excipient.

In one embodiment, the composition is a liquid formulation, preferably an aqueous solution. In another embodiment, the composition is suitable for pharmaceutical use, for example a pharmaceutical composition comprising a pharmaceutically acceptable carrier or diluent.

In one embodiment, the composition is a pharmaceutical composition comprising the at least one active ingredient, the at least one crystallizing excipient, and a pharmaceutically acceptable carrier. As used herein "pharmaceutically acceptable carrier" includes any and all solvents, dispersion media, coatings, and the like that are physiologically compatible. The type of carrier can be selected based upon the intended route of administration. In some embodiments, the carrier is suitable for administering by way of, but not limited to, intravenous, inhalation, parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal means. Pharmaceutically acceptable carriers include, but are not limited to, sterile aqueous solutions or dispersions for the preparation of sterile injectable solutions or dispersion.

Active Ingredient

In some embodiments, the at least one active ingredient can be any active ingredient, including, but not limited to, proteins, nucleic acids, and combinations thereof. Proteins can include, but are not limited to, glycoproteins (e.g. ATIII), clotting factors, growth factors, cytokines, antibodies, and chimeric constructs. The term "protein" herein is intended to be broad and refers to individual or collective native human or other mammalian proteins; and/or homogenous or heterogeneous distribution of polypeptides arising from a single or multiple gene products; and/or fragments of proteins displaying a particular activity; and/or such proteins and/or active fragments thereof produced by recombinant techniques including transgenic technology.

In some embodiments, the at least one active ingredient is a protein. In one embodiment, the protein is AT III. In other embodiments, the composition comprises only one active ingredient, wherein the active ingredient is AT III. In another embodiment, the AT III is the only active ingredient in the composition, however, the composition comprises other proteins including non-AT III proteins and/or inactive forms of AT III. For example, functional AT III may be a percentage of the total protein content of the composition.

The term "AT III," as used herein, is intended to be broad unless specifically stated otherwise. For example, the term refers to all naturally occurring polymorphs of AT III. The term also includes functional fragments of AT III, chimeric proteins comprising AT III or functional fragments thereof, homologs obtained by analogous substitution of one or more amino acids of AT III, and species homologs. The term also refers to all AT III polypeptides that are a product of recombinant DNA technology including an AT III that is a product of transgenic technology. For example, the gene coding for AT III can be inserted into a mammalian gene encoding a milk whey protein in such a way that the DNA sequence is expressed in the mammary gland as described in, e.g., U.S. Pat. No. 5,322,775, which is herein incorporated by reference for its teaching of a method of producing a proteinaceous compound. The term also refers to all AT III proteins synthesized chemically by methods known in the art such as, e.g., solid-phase peptide synthesis. The term also refers to AT III prepared from plasma. The term also refers to AT III that can be obtained commercially. The AT III can correspond to a human or a non-human AT III.

In one embodiment, the AT III is plasma-derived AT III. In another embodiment, the AT III is prepared from a plasma fraction paste. In other embodiments, the AT III is prepared from an albumin-depleted plasma fraction or a pre-purified AT III preparation fraction. U.S. Pat. No. 5,561,115 to Tenold is herein incorporated by reference for its teaching of a method of preparing AT III from serum or plasma.

In other embodiments, the AT III is recombinant AT III. Production of recombinant proteins including recombinant AT III is described in, e.g., U.S. Pat. Nos. 4,517,294, 4,632,981, 4,873,316, 5,420,252, 5,618,713, 5,700,663, 5,843,705, 6,441,145, 6,878,813, 7,019,193, Fan et al., JBC, 268:17588 (1993), Garone et al., Biochemistry, 35:8881 (1996), International Publication No. WO02/02793; U.S. Publication Nos. US2003/096974 and US2006/0024793, and Gillespie et al., JBC, 266:3995 (1991), each of which is incorporated herein by reference for its teaching of production of recombinant proteins including recombinant AT III.

In one embodiment, the composition is characterized as comprising an AT III having a greater than 90% purity. In other embodiments, the AT III has a purity greater than 95%, preferably at least about 99%. In some embodiments, at least about 50%, illustratively, about 50% to about 100%, about 60% to about 90%, about 70% to about 80% of all AT III in the composition is active AT III.

In other embodiments, the composition to be lyophilized comprises at least about 0.1 mg/ml AT III, illustratively, about 0.1 to about 100 mg/ml, about 0.5 to about 50 mg/ml, about 1 to about 30 mg/ml, and about 5 to about 15 mg/ml AT III, wherein the AT III is a fraction or all of the total protein present in the composition.

In one embodiment, the composition comprises a therapeutically effective amount of AT III. A "therapeutically effective amount" refers to an amount effective, at dosages and for periods of time necessary, to achieve the desired therapeutic result, such as, for example, anticoagulation associated with hereditary antithrombin deficiency. A therapeutically effective amount of AT III can vary according to factors such as the disease state, age, sex, and weight of the individual subject, and the ability of the AT III to elicit a desired response in the subject. A therapeutically effective amount also can be one in which any toxic or detrimental effects of AT III are outweighed by the therapeutically beneficial effects.

In other embodiments, the composition comprises a prophylactically effective amount of AT III. A "prophylactically effective amount" refers to an amount effective, at dosages and for periods of time necessary, to achieve the desired prophylactic result, such as, for example, preventing or inhibiting thromboembolic episodes in subjects that have had multiple thromboembolic episodes, or patients who are at risk of further episodes. A prophylactically effective amount can be determined as described above for the therapeutically effective amount.

Crystallizing Excipient

In one embodiment, the at least one crystallizing excipient is selected from the group consisting of alanine, mannitol, glycine, and NaCl.

In some embodiments, the at least one crystallizing excipient is present in the composition in a total crystallizing excipient amount of at least about 0.01% (w/v), illustratively, about 0.01% to about 10%, about 0.1% to about 5%, and about 0.7% to about 1.8% (w/v).

In other embodiments, the lyophilized product comprises at least about 20% (w/v) total crystallizing excipient, illustratively, about 20 to about 80%, about 30 to about 70%, and about 36 to about 60% (w/v) total crystallizing excipient.

In some embodiments, the at least one crystallizing excipient is alanine and NaCl. In one embodiment, the NaCl is present in an amount of about 50 mM to about 300 mM, preferably about 100 mM to about 250 mM. In one embodiment, sodium chloride itself can be used without any of the aforementioned crystallizing excipients, in which case it can be included in the formulation in an amount of about 300 mM or greater. In other embodiments, the composition (e.g., aqueous pharmaceutical formulation) is a hypertonic solution.

In addition to the at least one active ingredient and the at least one crystallizing excipient, the composition also can further comprise one or more other excipients, i.e., one or more other substances used in combination with the active ingredient to constitute the composition. Some non-limiting examples of the one or more other excipients include stabilizing agents, buffering agents, divalent cations (e.g., calcium salts), binders, lubricants, disintegrants, diluents, colorants, flavors, glidants, surfactants, absorbants, and sweetening agents.

The combinations of active ingredients and excipients in accordance with the present invention can provide stability of an active ingredient in lyophilized preparations; however, the compositions of the present invention also can exhibit a degree of stability in the liquid or semi-liquid state as well.

In other embodiments, the composition further comprises a stabilizing agent. For example, the stabilizing agent can be selected from the group consisting of sucrose, mannitol, and trehalose. Prior to lyophilization, the stabilizing agents can be present in the composition in a total stabilizing agent amount of at least about 1%, illustratively, about 1% to about 4% and about 2% to about 3%. In some embodiments, the stabilizing agent is present in the composition in an amount of about 2%.

A buffer also can be present in the compositions of the present invention, in particular where the active ingredient is susceptible to being adversely affected by pH shifts during lyophilization. The pH should preferably be maintained in the range of about 6 to 8 during lyophilization, and more preferably at a pH of about 7. The buffering agent can be any physiologically acceptable chemical entity or combination of chemical entities which have the capacity to act as buffers including, but not limited to, phosphate buffer, citrate buffer, acetate buffer, citric acid/phosphate buffer, histidine, tris-(hydroxymethyl)-aminomethane (Tris), 1,3-bis[tris-(hydroxy-methyl)methylamino]-propane (BIS-Tris Propane), piperazine-N,N-bis-(2-ethanesulfonic acid) (PIPES), 3-{N-morpholino)propanesulfonic acid (MOPS), N-2-hydroxyethyl-piperazine-N'-2-ethanesulfonic acid (HEPES), 2-(N-morpholino)ethanesulfonic acid (MES), and N-2-acetamido-2-aminoethanesulfonic acid (ACES).

In one embodiment, the buffering agent is included in the composition in a concentration of about 10 to about 50 mM. When histidine is added to the compositions, concentrations of at least about 20 mM, preferably about 25 mM can be used, alone or in combination with other buffers such as Tris.

In other embodiments, the composition further comprises a divalent cation, for example a calcium salt. In one embodiment, the calcium salt is present in an amount of about 1 mM to about 5 mM.

In one embodiment, the composition further comprises a surfactant. The surfactant can be present in an amount of about 0.1% or less. Non-limiting examples of surfactants include POLYSORBATE 20 (e.g., TWEEN® 20), POLYSORBATE 80 (e.g., TWEEN® 80), polyoxyethylene (80) sorbitan fatty acid ester, pluronic polyols (e.g., F-38, F-68), and polyoxyethyleneglycol dodecyl ethers (e.g., Brij-35).

In accordance with the present invention, the composition also can further comprise an antioxidant. The antioxidant can be present in the composition in a total amount of at least 0.05 mg/ml, illustratively, about 0.05 to about 50 mg/ml, about 0.1 to about 10 mg/ml, and about 1 to about 5 mg/ml. Non-limiting examples of antioxidants include N-Acetyl-L-Cysteine/Homocysteine, glutathione, 6-hydroxy-2,5,7,8-tetramethylchroman-2-carboxylic acid (Trolox), lipoic acid, methionine, sodium thiosulfate, platinum, glycine-glycine-histidine (tripeptide), and butylatedhydroxytoluene (BHT). In some embodiments, the composition further comprises glutathione in an amount of about 0.05 mg/ml to about 5 mg/ml.

The compositions of the present invention also can comprise calcium or another divalent cation, in particular where the cation provides for interaction with the active ingredient to maintain its activity. In one embodiment, the composition further comprises a divalent cation. In another embodiment, the divalent cation is provided as a calcium salt, for example calcium chloride, but can also be other calcium salts such as calcium gluconate, calcium glubionate, or calcium gluceptate. In some embodiments, the calcium salt is present in an amount of about 1 mM to about 5 mM. In other embodiments, the calcium salt is present in an amount of about 3 mM to about 4 mM, preferably about 4 mM.

In some embodiments, the combination of histidine and glutathione can produce synergistically beneficial effects on the stability of a particular active ingredient present in a composition. For example, histidine, while acting as a buffer, also can act as a metal chelator. To the extent that level of activity of the active ingredient is believed to be affected by metal-induced oxidation, for example, histidine can therefore act to stabilize binding by oxidizing metal ions. It is believed that by binding these metals, the glutathione (or any other antioxidant present) is thereby able to provide further antioxidative protection, since the oxidative effect of the metal ions bound by the histidine has been contained. Other chelating agents also can be included in the compositions/formulations of the present invention. Such chelating agents preferably bind metals such as copper and iron with greater affinity than calcium, for example where a calcium salt is being used in the composition. One example of such a chelator is deferoxamine, which is a chelating agent that facilitates the removal of $Al^{++}$ and iron.

Lyophilization

Generally, specific temperatures and/or temperature ranges of a lyophilization method refer to the shelf temperature of the lyophilizer equipment, unless otherwise noted. The shelf temperature refers to the control temperature for coolant flowing through the shelves of the lyophilizer, which is typically what one controls in terms of temperature during lyophilization. The temperature of the sample (i.e., the product temperature) depends on the shelf temperature, the chamber pressure and/or the rate of evaporation/sublimation during primary drying (evaporative cooling makes product temperatures less than the shelf temperature).

A. Freezing

In one embodiment, the first temperature is about −48° C. or below. In another embodiment, the first temperature is about −54° C. or below. In other embodiments, the period of time is at least about 30 minutes, illustratively, about 30 minutes to about 20 hours, about 1 to about 18 hours, about 2 to about 16 hours, about 3 to about 14 hours, about 4 to about 10 hours, about 5 to about 8 hours, and about 6 to about 7 hours. In one embodiment, the period of time is about 6 hours.

The temperature and the period of time can depend on factors such as the volume of the solution per vial, independent of the composition to be lyophilized.

The present invention sometimes refers to the objective of complete or 100% excipient crystallization, and one skilled in the art understands that "complete crystallization" may be difficult to verify, in particular where the sensitivity of technology cannot inform one with absolute certainty that an excipient is completely or 100% crystallized. Therefore, in practical terms, the invention provides lyophilization methods that at least improve excipient crystallization in respect to prior methods. Accordingly, as used herein, "completely crystallized" products can be assessed, for example, by differential scanning calorimetry (DSC), where one skilled in the art recognizes that a non-reversible exothermic event on a first scan represents a crystallization event, which indicates that a crystallizing excipient did not completely crystallize during lyophilization. In some embodiments, the at least one crystallizing excipient is partially crystallized, wherein partially crystallized is characterized as a degree of crystallization of about 50% or more, illustratively, at least about 50%, at least about 60%, at least about 70%, at least about 80%, at least about 90%, at least about 95%, at least about 96%, at least about 97%, at least about 98%, at least about 99%, at least about 99.5%, at least about 99.8%, and less than 100%.

B. Annealing

In other embodiments, the method further comprises exposing the first composition to a second temperature for a second period of time to obtain a second composition, wherein the second temperature is above the first temperature.

In one embodiment, the second temperature is at least about 5° C. above the first temperature, illustratively, about 5° C. to about 30° C. and about 10° C. to about 20° C. above the first temperature. For example, wherein the first temperature is about −50° C., in some embodiments, the second temperature is about −30° C.

In some embodiments, the second period of time is at least 10 minutes, illustratively, about 10 minutes to about 10 hrs, about 30 minutes to about 8 hours, about 1 hour to about 6 hours, and about 2 hours to about 4 hours. In other embodiments, the second period of time is less than, greater than, or about equal to the first period of time.

Without being held to any particular theory, it is believed that such annealing steps can help to improve sublimation rates and/or decrease intra-batch heterogeneity depending on the conditions and the particular composition.

In some embodiment, an annealing step is optional.

In other embodiments, following the second period of time, the second composition is exposed to a third temperature for a third period of time, wherein the third temperature is below the second temperature. For example, in some embodiments, the third temperature is about the same as the first temperature. In other embodiments, the third temperature is at least 5° C. below the second temperature, illustratively, about 5° C. to about 30° C. and about 10° C. to about 20° C. below the second temperature. For example, wherein the second temperature is about −30° C., in some embodiments, the second temperature is about −50° C.

In some embodiments, the present invention provides a method of lyophilizing a composition comprising at least one active ingredient and at least one crystallizing excipient. The method comprises:
   (a) exposing the composition to a first temperature for a first period of time sufficient to obtain a first composition having the at least one crystallizing excipient partially or completely crystallized;
   (b) exposing the first composition to a second temperature for a second period of time to obtain a second composition, wherein the second temperature is above the first temperature; and
   (c) exposing the second composition to a third temperature for a third period of time to obtain a third composition, wherein the third temperature is below the second temperature.

In one embodiment, the period of time is at least about 30 minutes, illustratively, about 30 minutes to about 20 hours, about 1 to about 18 hours, about 2 to about 16 hours, about 3 to about 14 hours, about 4 to about 10 hours, about 5 to about 8 hours, and about 6 to about 7 hours. In another embodiment, the period of time is about 6 hours. In other embodiments, the period of time is about 3 hours. In other embodiments, the third period of time is less than, greater than, or about equal to the first period of time. In still further embodiments, the conditions (e.g., temperature and time) in step (a) and (b) are the same or substantially the same.

C. Drying

In other embodiments, the methods of the present invention further comprise a drying phase. The drying phase can comprise a primary drying phase and a secondary drying phase.

Accordingly, in some embodiments, the present invention provides a method for lyophilizing a composition comprising at least one active ingredient and at least one crystallizing excipient. The method comprises:
   (a) exposing the composition to a first temperature for a first period of time sufficient to obtain a first composition having the at least one crystallizing excipient partially or completely crystallized; and
   (b) drying the first composition to form a lyophilized cake.

In other embodiments, the present invention provides a method for lyophilizing a composition comprising at least one active ingredient and at least one crystallizing excipient, the method comprising:

(a) exposing the composition to a first temperature for a first period of time sufficient to obtain a first composition having the at least one crystallizing excipient partially or completely crystallized;

(b) exposing the first composition to a second temperature for a second period of time to obtain a second composition, wherein the second temperature is above the first temperature;

(c) exposing the second composition to a third temperature for a third period of time to obtain a third composition, wherein the third temperature is below the second temperature; and (d) drying the third composition to form a lyophilized cake.

In one embodiment, drying comprises a primary drying step. The primary drying can remove the frozen water (sublimation of ice). Preferably, unbound or easily removable ice is removed from the sample by the primary drying. The unbound water at the beginning of the primary drying step can preferably be in the form of free ice, which can be removed by sublimation, i.e., converting it directly from a solid to a vapor.

In some embodiments, the primary drying step can be conducted at a temperature of about −35° C. to about 20° C., or about −25° C. to about 10° C., or about −20° C. to about 0° C. In one embodiment, the primary drying step is conducted at about 0° C. In other embodiments, the primary drying step can be performed for a total time of at least about 1 hour, illustratively, about 1 hour to about 1 week, about 10 hours to about 4 days, and about 20 hours to about 40 hours. In another embodiment, the primary drying step comprises drying the first or the third composition under a pressure of about 0 to about 200 mTorr, preferably about 100 mTorr, at a temperature of about −50° C. for about 1 hour followed by 0° C. for about 35 hours.

An optional "primary drying ramp" step (i.e., the increase of temperature from the step prior to primary drying to the primary drying temperature) can be performed in accordance with the methods of the present invention at a rate of about 0.1° C. to about 10° C. per minute.

The primary drying step can be conducted for a time sufficient to ensure that substantially all of the frozen water is removed from the sample. One skilled in the art understands that the primary drying time varies with configuration, in that the duration of primary drying can depend on the fill volume and geometry (surface area of the cake—resistance/flux). In one embodiment, the duration of primary drying is at least about 5 hours, illustratively, about 5 hours to about 100 hours, about 10 hours to about 80 hours, about 30 hours to about 60 hours, and about 40 to about 50 hours.

Primary drying can be monitored by any number of methods including observing the changes in product temperature during freeze-drying. Another method is to observe the changes in chamber pressure, where when sublimation ends, no more water molecules are in the chamber contributing to changes in pressure. The end of the primary drying step can be determined to be when the product (sample) temperature approaches the shelf-temperature, for example evidenced by a significant change in the slope of the product temperature trace due to a reduced sublimation rate; when sublimation ends, evaporative cooling ends. To prevent a premature ending, in some embodiments, an extra 2 to 3 hours of primary drying can be added to the duration. Another method to monitor the completion of primary drying is the pressure rise test, where by disconnecting the vacuum source, the chamber pressure should rise at a rate depending on the amount of moisture in the product. In one embodiment, the end of the primary drying process can be set as when the rate of pressure rise is below a specified value. Another method for determining the end of the primary drying step is the measurement of the heat transfer rate.

In other embodiments, directly prior to primary drying, the composition can be placed under vacuum at the temperature of the step directly prior to primary drying. Once initiated, the vacuum can be present for the remainder of the lyophilization process, although the vacuum level can change.

Further information on drying during lyophilization can be found in Carpenter, J. F. and Chang, B. S., Lyophilization of Protein Pharmaceuticals, Biotechnology and Biopharmaceutical Manufacturing, Processing and Preservation, K. E. Avis and V. L. Wu, eds. (Buffalo Grove, Ill. Interpharm Press, Inc.) (1996), which is incorporated herein by reference for its teaching of drying.

In one embodiment, drying further comprises one or more secondary drying steps to reduce moisture levels, preferably to levels that provide a desired biological and/or structural characteristic of the final product.

In some embodiments, each of the one or more secondary drying steps is conducted at a temperature that is about 0° C. or above, illustratively, about 0° C. to about 100° C., about 10° C. to about 90° C., about 20° C. to about 80° C., about 30° C. to about 70° C., about 40° C. to about 60° C., and about 45° C. to about 50° C. In one embodiment, the secondary drying step comprises a first, a second, and a third secondary drying step performed at about 40° C., about 45° C., and about 50° C., respectively. In one embodiment, the secondary drying step comprises a temperature of about 35° C. for a period of time of about 16 hours.

The step of increasing the temperature to the one or more secondary drying steps is herein referred to as the "secondary drying ramp," which can be optional. The secondary drying ramp can be performed at a rate of temperature increase of about 0.1° C. to about 10° C. per minute.

Each of the one or more secondary drying steps can be conducted for a time sufficient to reduce the residual moisture level in the lyophilized product to a final level. In some embodiments, the final residual moisture level is about 10% or less, illustratively, about 9% or less, about 8% or less, about 7% or less, about 6% or less, about 5% or less, about 4% or less, about 3% or less, about 2% or less, about 1% or less, about 0.8% or less, about 0.6% or less, about 0.5% or less, about 0.2% or less, and about 0.1% or less.

In one embodiment, the secondary drying step is conducted at about 35° C. In other embodiments, the secondary drying step can be performed for a total time of at least about 1 hour, illustratively, about 1 hour to about 1 week, about 10 hours to about 4 days, and about 16 hours to about 40 hours. In another embodiment, the secondary drying step comprises drying under a pressure of about 0 to about 200 mTorr, preferably about 100 mTorr, at a temperature of about 35° C. for about 16 hours.

To determine the residual moisture level in a sample, the Karl Fischer method can be used, for example. Further, the pressure rise test or the measurement of the heat transfer rate also can be used to determine the end of each of the one or more secondary drying steps. Alternatively, an electronic hygrometer or a residual gas analyzer also can be used. Also, the minimum duration of the one or more secondary drying steps can be determined using different combinations of shelf temperatures (where the shelf temperature of the one or more secondary drying steps is the same or less than the temperature used in the high-temperature step) and durations.

Residual moisture content can be determined by several methods, including loss-on-drying, Karl Fischer titration, thermal gravimetric analysis (TGA), gas chromatography (GC), or infrared spectroscopy.

Without being held to any particular theory, it is believed that during lyophilization, the active ingredient is converted from being in an aqueous phase to being in an amorphous solid phase, which is thought to protect the active ingredient from chemical and/or conformational instability. The lyophilized preparation not only contains an amorphous phase, but also includes a component that crystallizes during lyophilization. This can provide lyophilization of the active ingredient and formation of a more elegant cake (e.g., a cake with minimal shrinkage from the sides of the container in which it was lyophilized).

In one embodiment, the lyophilized cake is characterized as being less than 50% collapsed. In another embodiment, the lyophilized cake is characterized as being about 0% to about 24% collapsed.

In another aspect, the present invention provides a method of lyophilizing an aqueous pharmaceutical formulation comprising AT III, the method comprising:

(a) exposing the formulation to a temperature below about −45° C. for a period of time sufficient to obtain a first composition having at least one crystallizing excipient partially or completely crystallized; and (b) drying the first composition to form a lyophilized cake.

In other aspects, the present invention provides a method of lyophilizing an aqueous pharmaceutical formulation comprising AT III, the method comprising:

(a) exposing the formulation to a freezing temperature below about −50° C. for a period of time sufficient to obtain a first composition having at least one crystallizing excipient partially or completely crystallized; and (b) drying the first composition to form a lyophilized cake. In some embodiments, the method, optionally, further comprises an annealing step wherein the formulation is exposed to an annealing temperature that is above the freezing temperature.

In another aspect, the present invention provides a method of lyophilizing an aqueous pharmaceutical formulation comprising AT III, the method comprising:

(a) exposing the formulation to a temperature below about −60° C. for a period of time sufficient to obtain a first composition having at least one crystallizing excipient partially or completely crystallized; and (b) drying the first composition to form a lyophilized cake.

Also provided are compositions (e.g., crystallized and/or lyophilized pharmaceutical compositions and cakes) prepared in accordance with the methods of the present invention.

Accordingly, in some embodiments, the present invention provides a lyophilized ATIII composition or cake prepared in accordance with the present invention.

In other embodiments, the methods of the present invention provide for products that at least maintain or substantially maintain the potency of the active ingredient(s) following storage of the lyophilized product. In one embodiment, the potency of the active ingredient(s) is maintained or substantially maintained after storage of the lyophilization product at about 5° C., about 25° C., or about 40° C. for about 1, about 2, about 3, or about 6 or more months. In another embodiment, after storage of the lyophilized product, the potency of the active ingredient is at least about: 70%, 80%, 90%, 95%, 99% and 100% relative to its pre-lyophilization potency.

Kits

In still further aspects, also provided are kits comprising the pharmaceutical compositions of the present invention, wherein the kit further comprises a dry and a liquid component, wherein the dry and liquid components can be present in separate containers in the kit, or some of the components can be combined into one container, such as a kit wherein the dry components are present in a first container and the liquid components are present in a second container, where the containers may or may not be present in a combined configuration. Optionally, the kits can further comprise a number of additional reagents. Optionally, the kits can further include instructions for using the components of the kit including, for example, instructions for reconstituting the lyophilized composition with an appropriate diluent. The instructions can be present in the kits as a package insert, in the labeling of the container of the kit or components thereof.

The present invention will be illustrated in more detail by way of Examples, but it is to be noted that the invention is not limited to the Examples.

EXAMPLES

Example 1

To determine freezing conditions that promote crystallization of the components in an AT III solution and improve the physical appearance of the finished product, lyophilization was performed on AT III formulations containing human plasma-derived AT III (6.88 mg/ml), alanine (100 mM), and NaCl (150 mM). Both alanine and NaCl are crystalline excipients. For this formulation, the physical appearance can be directly related to the crystallinity of the excipients. It was desirable to crystallize NaCl and alanine as completely as possible during freezing in order to provide a solid matrix to support cake structure.

Differential Scanning calorimetry: Freeze-thawing thermal events of AT III formulation were investigated with a differential scanning calorimeter (Model 2920, TA instruments, Inc., New Castle, Del.). The temperature and cell constant of the DSC were calibrated according to standard procedure using high-purity indium. Modulated DSC was used to study the heat flow and heat capacity (Cp) change of the maximally freeze-concentrated solutes. The runs were made with amplitude of 0.5° C. at a period of 80 sec. The sample, 20 microliter, was sealed in an aluminum hermetic pan and scanned through a sub-zero temperature range.

Thermal events in NaCl, Alanine and AT III reconstituted solution: Crystallization and melting events were investigated in NaCl, alanine and AT III reconstituted solution.

DSC Experimental Design by E-CHIP: A DOE designed by Echip was performed to evaluate the effects of freezing temperature, freezing hold time and annealing hold time on the crystallization of excipients. Freezing (from 5° C. to freezing temperature) ramp rate was set as 2° C./min. After annealing, the product was frozen from −30° C. to freezing temperature at 5° C./min. Warming ramp rate was fixed as 1° C./min.

The effect of ramp rates on crystallization: Different cooling rates (2° C./min vs. 0.2° C./min) were compared to investigate the effect of ramp rates on crystallization. Various ramp rates during annealing (5° C./min vs. 0.2° C./min, 1° C./min vs. 0.2° C./min) were also evaluated.

The formation of condensed phase: During the process of supercooling, molecular conformations and configurations that are available in the liquid phase but not in a crystalline solid phase are frozen in. This process of 'trapping' conformations and configurations during cooling occurs when the rate of viscosity increase exceeds the rate of molecular re-orientation. The 'freezing in' of conformational states results in a condensed phase that will have some degree of short-range molecular order but, similar to the liquid, will lack the long-range molecular order characteristics of a crystalline solid PI.

The formation of condensed phase was observed by modulated DSC where the heat capacity (Cp) of freeze-concentrated amorphous phase decreased continuously until equilibrium was reached. Cp is an intrinsic property and is directly related to molecular mobility. Greater Cp means more mobility and smaller Cp indicates less mobility. A material in liquid state has a greater Cp than its solid counterpart. The decrease in Cp is due to the physical transformation of a material from a more fluid state to a solid state.

Cp was monitored using the freezing and annealing protocol shown in Table 1.

TABLE 1

AT III lyophilization cycle for first run.

| Step | Ramp Time (Time) Target | Shelf Temp (° C.) Target | Shelf Temp (° C.) Range | Hold Time (min) Target | Pressure (mTorr) Target | Pressure (mTorr) Range |
|---|---|---|---|---|---|---|
| Loading | N/A | 5 | ±3 | Until loading Is complete | Atmospheric | |
| Freezing | N/A | 5 | ±3 | 120 | Atmospheric | |
| | 150 | −25 | ±3 | 60 | Atmospheric | |
| | 240 | −52 | ±3 | 120 | Atmospheric | |
| Annealing | 90 | −30 | ±3 | 60 | Atmospheric | |
| | 180 | −52 | ±3 | 120 | Atmospheric | |
| Evacuation | Until pressure Is controlled | −52 | +3 | 60 | 100 | +50 |
| Primary Drying | 240 | 0 | ±3 | 1920 | 100 | ±50 |
| Secondary Drying | 180 | 35 | ±3 | 840 | 100 | ±50 |

The solution was frozen from 0 to −52° C. and held for 120 min. It was then warmed up to −30° C. and held for 1 hr. Finally, the product was frozen again to −52° C. for another 2 hrs and then ramped up to 0° C. The first freezing rate was 0.2° C./min. The effect of freezing hold time (2 hr, 5 hr and 10 hr) and temperature (−46° C., −48° C. and −52° C.) on the Cp was also evaluated.

Freeze-drying: Most of the experiments were done in the Lyostar II FTS system (SP Industries). Some were conducted in the Minilyo freeze dryer (Usifroid). The freezing techniques are listed in Table 2.

TABLE 2

Freezing technique.

| Technique | Freezing temperature (° C.) | Freezing hold time (hr) |
|---|---|---|
| 1 | −52 | 2 |
| 2 | −54 | 2 |
| 3 | −54 | 6 |
| 4 | −50 | 6 |
| 5 | −60 | 6 |
| 6 | −52 | 15 |

Techniques 1 to 5 differ in shelf temperature and hold time for the first freezing stage. The second freezing temperature was set the same as the first freezing temperature. And the hold time for the second freezing was 2 hrs. Technique 6 specifies the condition that the product was frozen at −52° C. for 2 hrs, annealed at −30° C. for 1 hr and frozen again to −52° C. for another 15 hrs. Annealing, primary and secondary drying were the same for all the cycles as listed in Table 1.

Scanning Electron Microscope (SEM): An SEM (Hitachi, Model S-3200, NCSU) was used to examine the morphologies of the freeze-dried cakes. The images of the sample at the surfaces or below the surfaces were displayed at magnification of 50 to 5000 times. Because the freeze-dried cakes were good electrical insulators, they charged upon exposure to the electron beam. This resulted in loss of resolution. To reduce the charging effects on exposure of the samples to the electric beam, all samples were coated with a thin layer of gold by sputtering using a bench top Denton Vacuum. The images of a collapsed cake, a solid cake, NaCl crystal and alanine crystal were taken.

Powder X-ray diffraction: Powder X-ray diffraction (XRD) was applied to characterize the crystallinity of a collapsed cake (ETP 5807) and a solid cake (ETP 5807 26N9540). XRD patterns were recorded by using a diffractometer (Rigaku, model Multiflex) with copper Kα radiation at 40 kV and 40 mA. The scans were conducted in the 2θ range from 10° to 90°. The scan speed was 1°/min for NaCl sample and 0.125°/min for alanine, ETP 5807.

Results and Discussion:

DSC work was aimed at characterizing the critical factors that govern the crystallization properties of excipients in the AT III formulation, Crystallization temperature (Tx), eutectic melting temperature (Te) and percent crystallization were determined.

Figure 2:
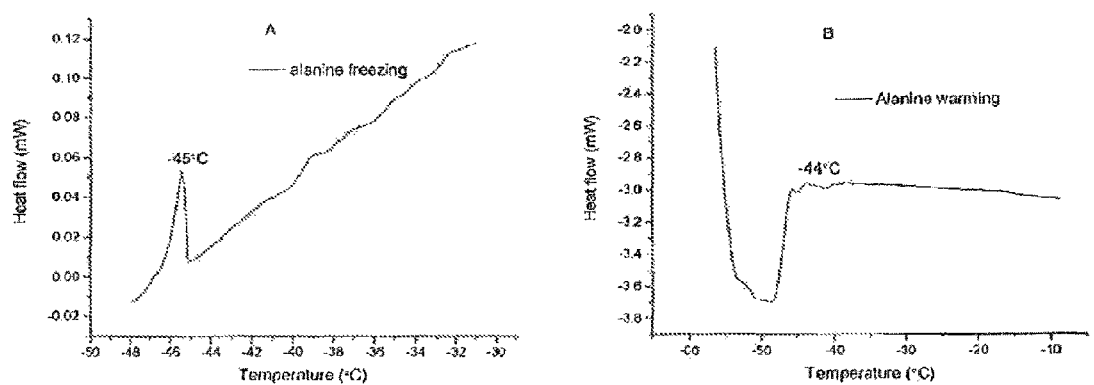
FIG. 2. DSC thermograms during freezing (A) and warming (B) of alanine solution (0.1M).

Crystallization and melting of NaCl, alanine and AT III solution: For NaCl neat solution, the exothermic crystallization peak occurred at approximately −38° C. during the freezing and the endothermic melting peak appeared at −19° C. during the warming (FIG. 1). The heat of fusion for the melting peak was determined to be 7.4 J/g. The thermogram for the alanine solution exhibited an exothermic peak at −45° C. during freezing indicating crystallization. During warming, however, there was a group of small peaks occurred at approximately at −44° C. The origin of these peaks was difficult to determine (FIG. 2).

Figure 3:
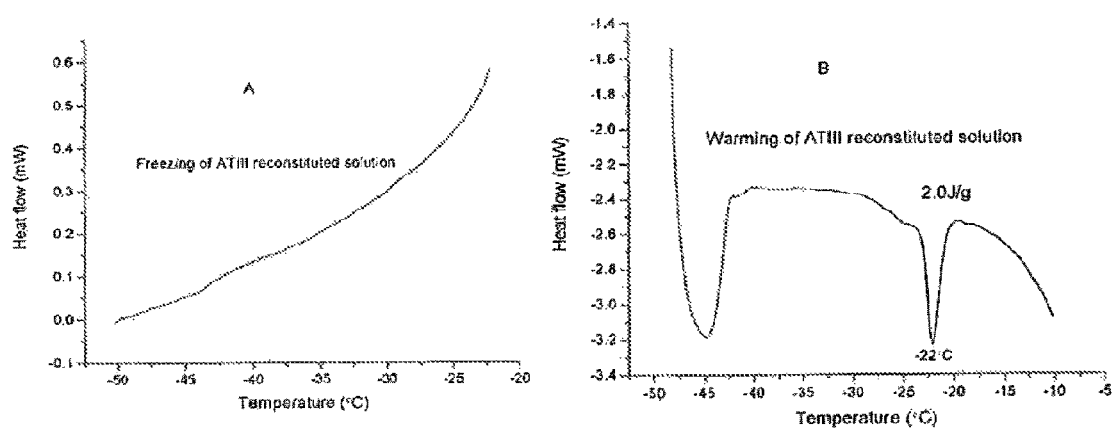
FIG. 3. DSC thermograms during freezing (A) and warming (B) of AT III reconstituted.

When the reconstituted AT III solution was analyzed, there was no evidence of exothermic activity observed during freezing. However, an eutectic melting peak was seen at −22° C., most likely due to the NaCl (FIG. 3). The heat of fusion (2.0 J/g) was smaller than the NaCl neat solution. The reduction in the heat of fusion could be attributed to the partial crystallization of NaCl in the AT III formulation. Based on this correlation, the percent crystallization was calculated by dividing the heat of fusion obtained from the formulations by a constant 7.4 J/g which is the heat of fusion for the NaCl neat solution.

DOE results: A DOE designed by ECHIP using central composite cube model was performed to evaluate the effects of freezing temperature, freezing hold time and annealing hold time on the crystallization of the AT III solution (Table 3).

TABLE 3

Crystallization profile.

| Trial | Freezing temperature (° C.) | Freezing hold time (hr) | Annealing hold time (hr) | NaCl eutectic melting peak area (J/g) | NaCl crystallization percentage (%) |
|---|---|---|---|---|---|
| 1 | −44 | 5 | 5 | 0 | 0 |
| 2 | −60 | 5 | 5 | 1.47 | 19.9 |
| 3 | −52 | 0 | 5 | 0 | 0 |
| 4 | −52 | 10 | 5 | 5.45 | 73.55 |
| 5 | −52 | 5 | 0 | 2.81 | 37.99 |
| 6 | −52 | 5 | 10 | 5.20 | 70.15 |
| 7 | −60 | 10 | 10 | 4.30 | 58.05 |
| 8 | −44 | 10 | 10 | 3.77 | 50.90 |
| 9 | −60 | 0 | 10 | 0 | 0 |
| 10 | −44 | 0 | 10 | 0 | 0 |
| 11 | −60 | 10 | 0 | 2.01 | 27.12 |
| 12 | −44 | 10 | 0 | 0.11 | 1.53 |
| 13 | −60 | 0 | 0 | 0 | 0 |
| 14 | −44 | 0 | 0 | 0 | 0 |
| 15 | −52 | 5 | 5 | 4.12 | 55.58 |
| 16 | −52 | 5 | 5 | 4.88 | 65.87 |
| 17 | −52 | 5 | 5 | 4.62 | 62.39 |
| 18 | −52 | 5 | 5 | 4.72 | 63.72 |
| 19 | −52 | 5 | 5 | 4.89 | 65.98 |
| NaCl | | | | 7.407 | 100 |

Figure 4:
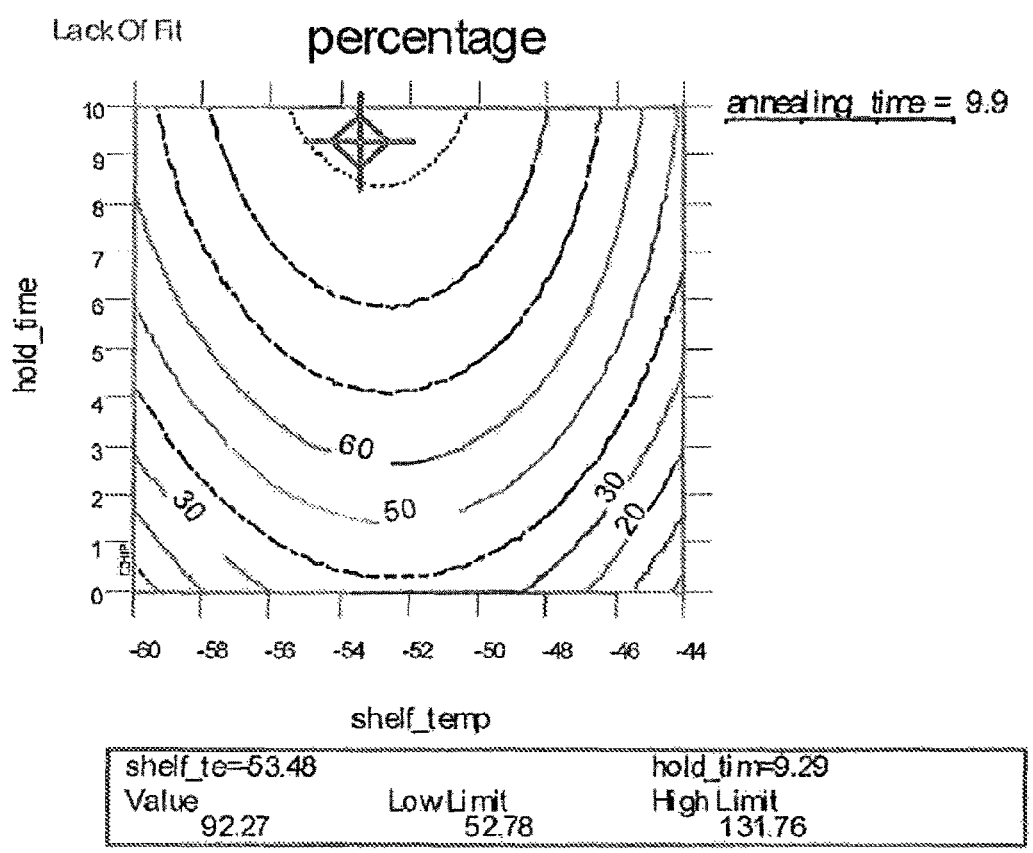
FIG. 4. The optimum crystallization conditions given by the DOE analysis.

The results from the DOE indicated that all variable conditions evaluated had a significant impact on the crystallization of the solution. Freezing at −52° C. produced a greater percentage of crystalline NaCl when compared to freezing at temperatures of −44° C. and −60° C. The decrease in crystallization at a lower temperature (−60° C.) can be explained by a trade-off between crystallinity and crystallization rate. Crystallinity was greater at lower temperature. However, the solution was so viscous that the crystallization rate was significantly reduced. DOE data analysis gave an optimum freezing temperature at −54° C. (FIG. 4).

An evaluation of the hold times indicates that the extension of freezing hold time and annealing hold time yields an increase in percent crystallization. DOE results suggest that the optimum hold time is 10 hr for both freezing and annealing (FIG. 4).

Data analysis also gives an out-of-fit message, indicating that the model generated by the E-CHIP might not fully reflect the crystallization process. Therefore, additional DSC work was performed to better understand the physical property change accompanied the crystallization process during freezing and annealing.

The effect of ramp rate on the crystallization: Cooling rate: As a plasticizer, water acts as a physical diluent that increases free volume and molecular mobility. It is the ability of water to increase molecular mobility that can promote diffusion-controlled processes such as crystallization. Rapid cooling traps more water within the amorphous phase whereas slowing cooling allows for the water to flow out of the system. Accordingly, rapid cooling promotes the formation of crystals. When the freezing rate was reduced from 2° C./min to 0.2° C./min, the NaCl percent crystallization was decreased by 82% (from 17% to 3%).

Ramp rate during annealing: When ramping from freezing to a warmer temperature, the molecular mobility is increased to such an extent that nucleation and crystallization occur. The ramp rate at this stage should be slow enough to produce sufficient crystals. The decrease in ramp rate from 1° C. to 0.2° C./min increased the percent crystallization from 38% to 95%. Further decrease in ramp rate to 0.1° C./min did not show much difference.

As ramped from −30° C. to −52° C., the decrease in the rate from 5° C./min to 0.2° C./min increased the crystallization 1.35 fold (from 17% to 39%). These results suggest that the 0.2° C./min ramp rate was appropriate for crystallization to occur.

Figure 5:
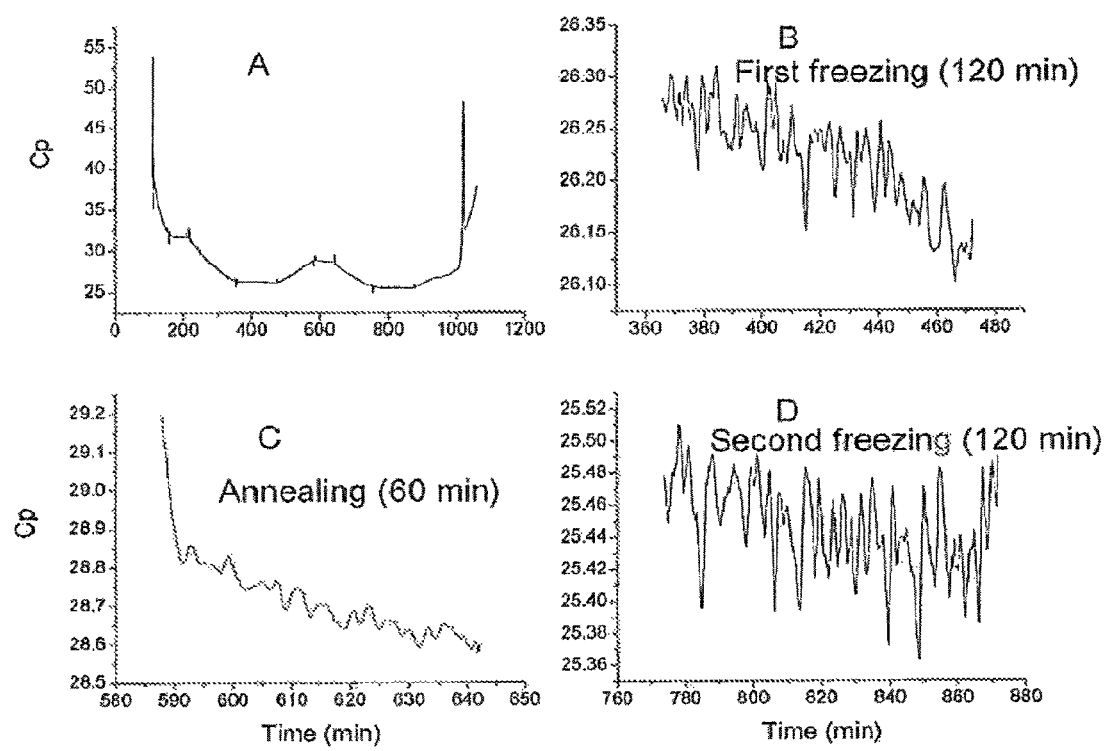
FIG. 5. A. Heat capacity (Cp) change during freezing and annealing by ETP-5807 cycle. B. Cp change during the first freezing. C. Cp change during annealing. D. Cp change during the second freezing.
Figure 6:
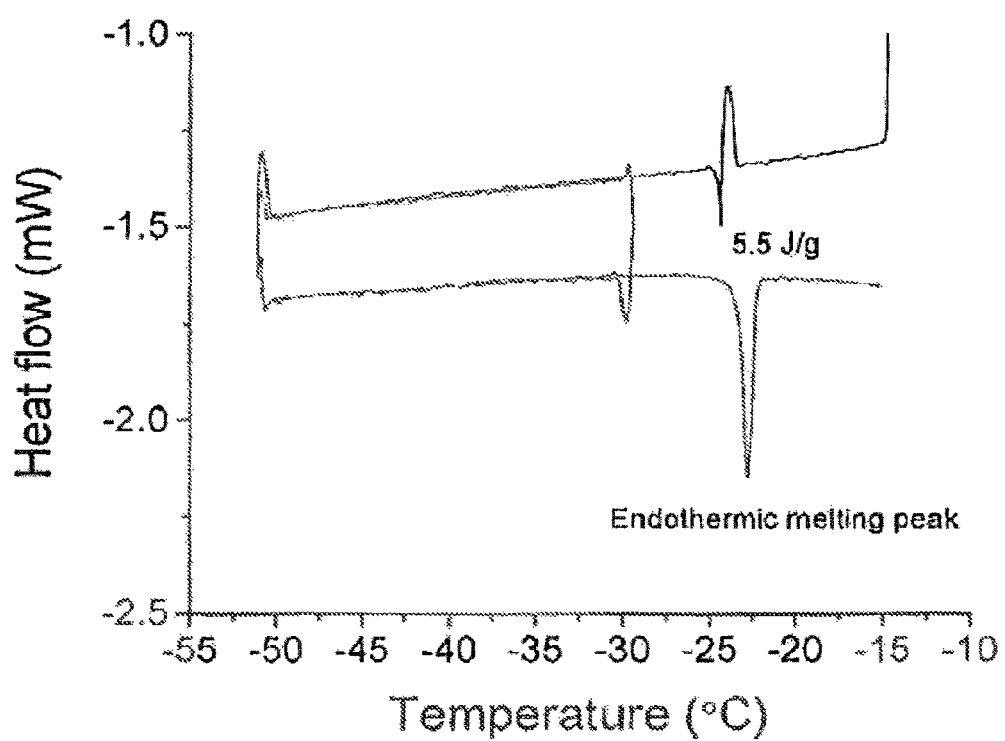
FIG. 6. Heat flow change with temperature by ETP-5807 cycle. The heat of fusion for the melting peak was determined to be 5.5 J/g.

Condensed phase and crystallization: Additional work was focused on the condensed phase and crystallization. FIG. 5A shows the Cp change with time by ETP-5807 cycle (Table 1). There is little change in Cp during first freezing (FIG. 5B), annealing (FIG. 5C) and second freezing (FIG. 5D). The formation of condensed phase is demonstrated by the Cp drop. Little change in Cp indicates little phase change occurs during freezing and annealing. Using these parameters, only 75% crystallization was obtained. The percent crystallization was calculated by dividing the heat of fusion which is 5.5 J/g (FIG. 6) by a constant 7.4 J/g which is the heat of fusion for the NaCl neat solution.

Figure 7:
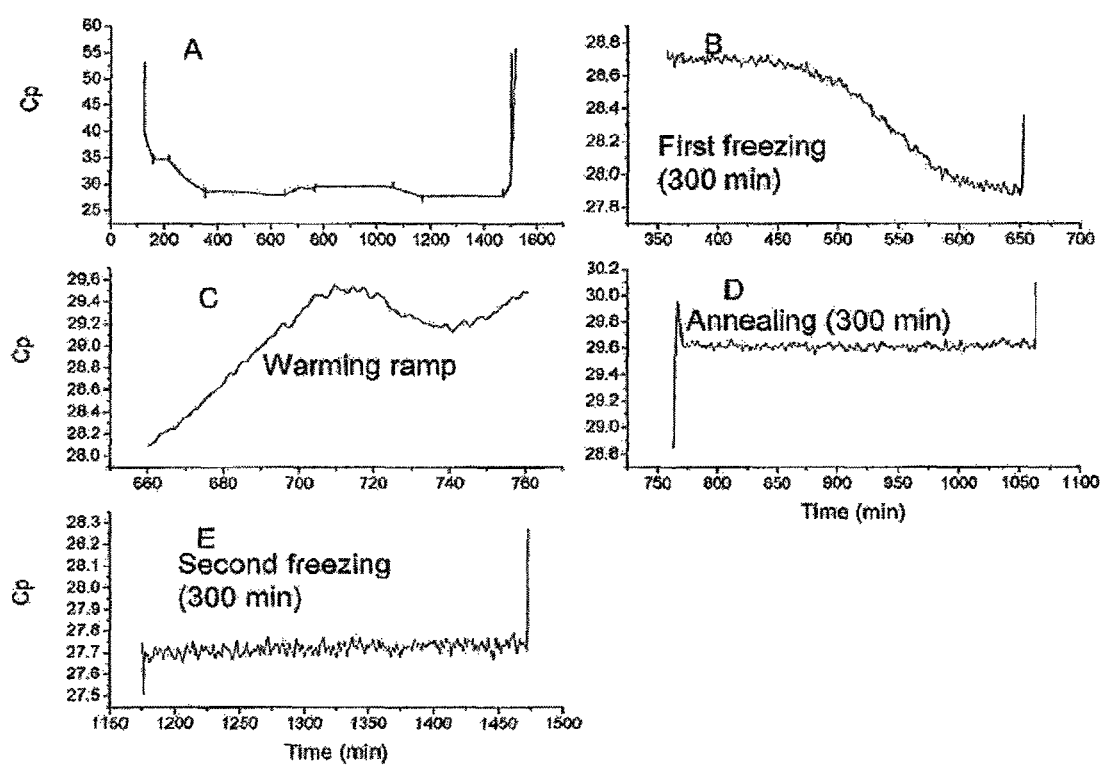
FIG. 7. A. Cp change during freezing and annealing by extending the freezing hold time to 5 hrs. B. Cp change during the first freezing. C. Cp change during warming ramp from −52° C. to −30° C. D. Cp change during the annealing. E. Cp change during second freezing.
Figure 8:
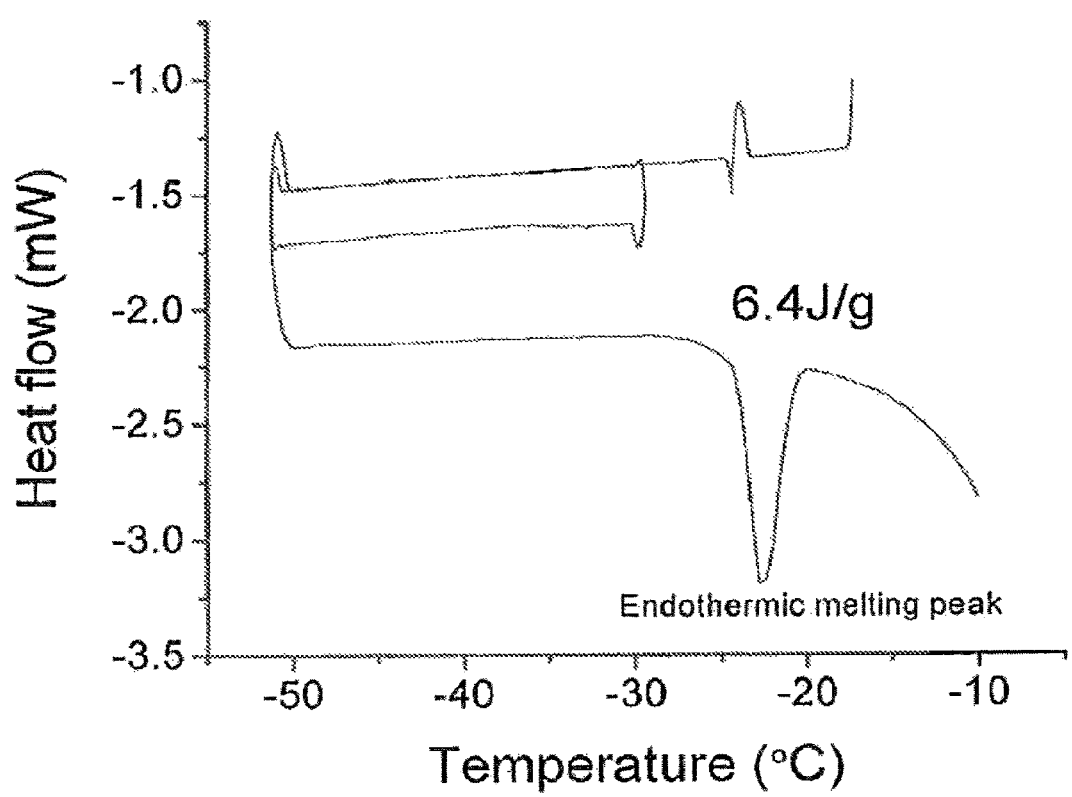
FIG. 8. Heat flow change with temperature, by extending the freezing hold time from 2 hrs to 5 hrs. The heat of fusion for the melting peak was determined to be 6.4 J/g.

The formation of condensed phase is observed with the extension of freezing hold time. FIG. 7A shows the whole picture of Cp change during freezing and annealing. When the first freezing hold time was extended from 2 hrs to 5 hrs, the Cp dropped to a minimum equilibrium value, indicative of the change from a more fluid phase to a more condensed phase (FIG. 7B). Further increase in the hold time from 5 hr to 10 hr did not illustrate a further decrease in Cp (data not shown). A crystallization peak was observed during the warming ramp (FIG. 7C). This unique peak was not present when the freezing hold time was only 2 hrs. If the solution has completely crystallized during the first freezing and warming ramp, it can be speculated that additional annealing or freezing would have little or no effect on the Cp. This was demonstrated by the fact that no change in Cp was observed during annealing and second freezing (FIGS. 7D and 7E). The percent crystallization was increased to 87% when extending the freezing time from 2 hrs to 5 hrs. Again, the percent crystallization was calculated by dividing the heat of fusion which is 6.4 J/g (FIG. 8) by the constant 7.4 J/g.

These results indicate that it requires 5 hrs at −52° C. for AT III amorphous phase to complete physical transformation. The condensed phase just starts to form if freezing for only 2 hrs. Sufficient freezing hold time is one prerequisite for crystallization.

Similar work was performed at temperatures warmer than −52° C. These results indicated that no crystallization activity when the product temperature was at −46° C. At a temperature of −48° C., when the hold time increased from 4 hrs to 5 hrs, the percent crystallization increased from 36% to 84%. Therefore, it is preferable that the AT III solution be frozen below −48° C. for at least 5 hrs in order to induce sufficient crystallization.

Lyophilization process development: In order to confirm the results from the DSC work on a macroscopic scale, four freezing temperatures (−50° C., −52° C., −54° C. and −60° C.) and two hold times (2 hrs and 6 hrs) were evaluated in a laboratory freeze-dryer.

Figure 9:
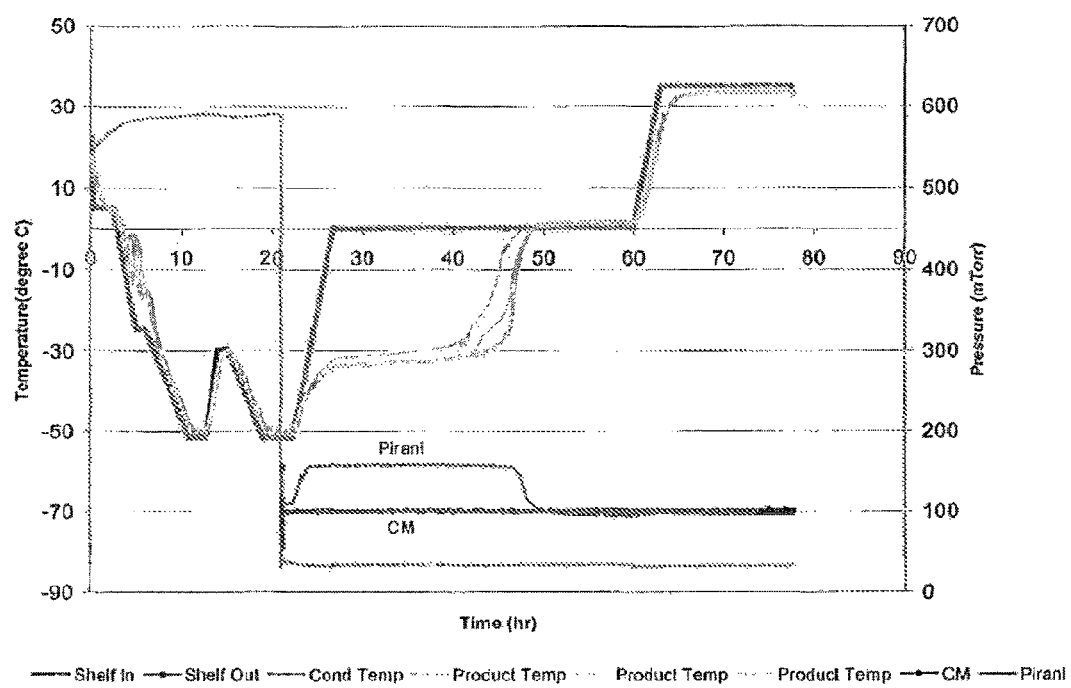
FIG. 9. AT III lyophilization profile by ETP-5807 cycle conducted in the lyostar II FTS unit.
Figure 10:
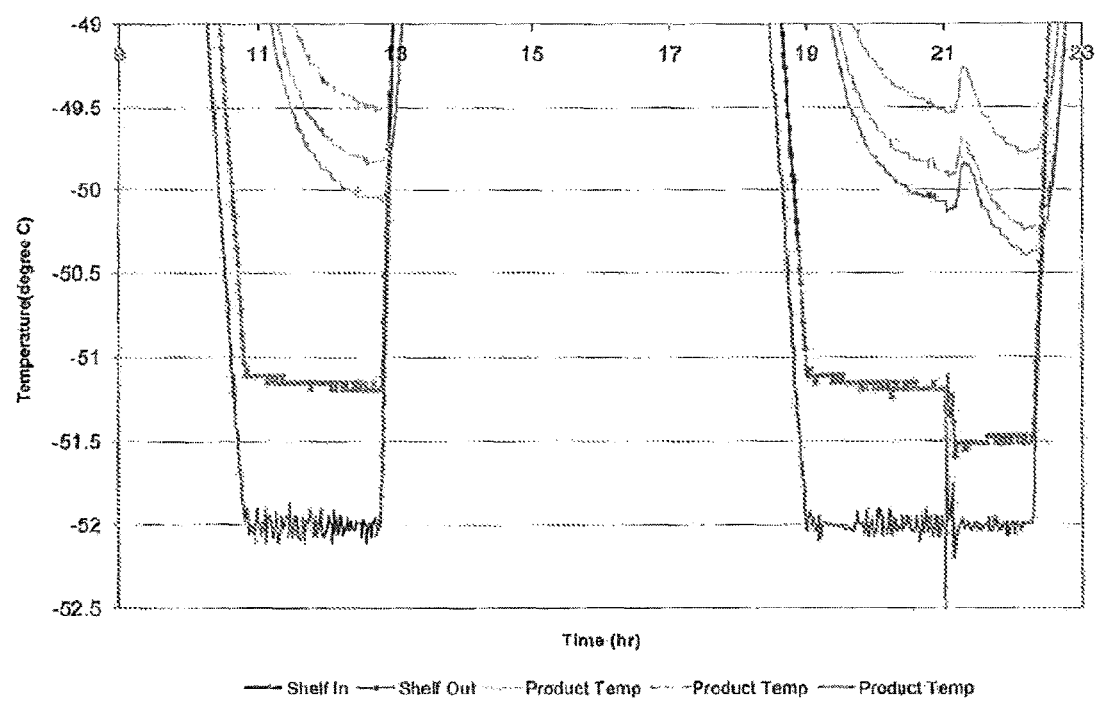
FIG. 10. Product temperature data during freezing by ETP-5807 cycle in FTS unit.

Freezing at −52° C. for 2 hrs: An initial evaluation of the current cycle parameters of Table 1 used during the execution of was performed using the Lyostar II FTS unit. The temperature and chamber pressure profile is presented in FIG. 9. The warmest product temperature measured by thermocouples during freezing process was approximately −49° C. (FIG. 10). After processing, the physical inspection revealed that only 2% of the cakes were acceptable, 17% had small holes, 57% partially collapsed and 23% were broken. Based on the DSC results, the product temperature (−49° C.) was cold enough to induce crystallization, however, the freezing hold time needs to be at least 5 hrs to form the condensed phase prior to the crystallization. The 2 hour freezing duration was too short to yield enough crystals.

Figure 11:
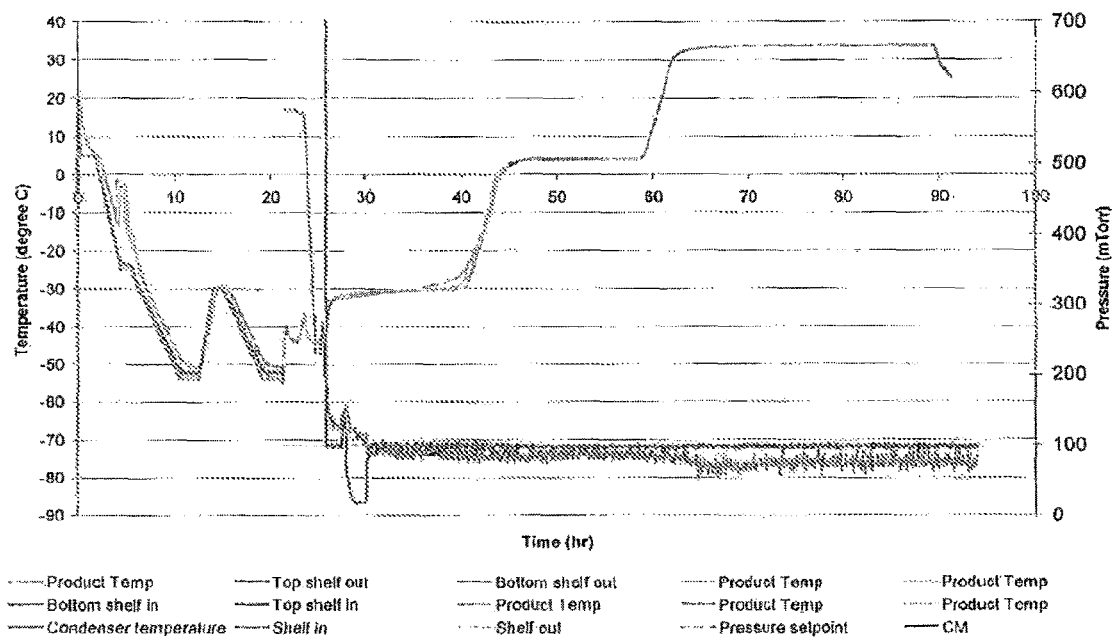
FIG. 11. AT III lyophilization profile when frozen at −54° C. for 2 hrs.
Figure 12:
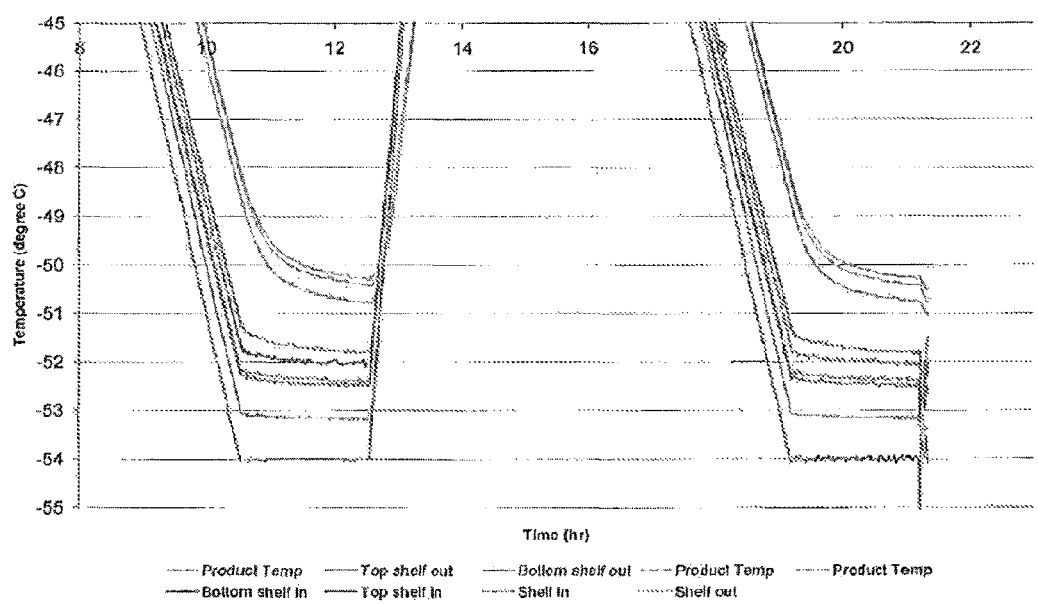
FIG. 12. Product temperature data when frozen at −54° C. for 2 hrs.
Figure 17:
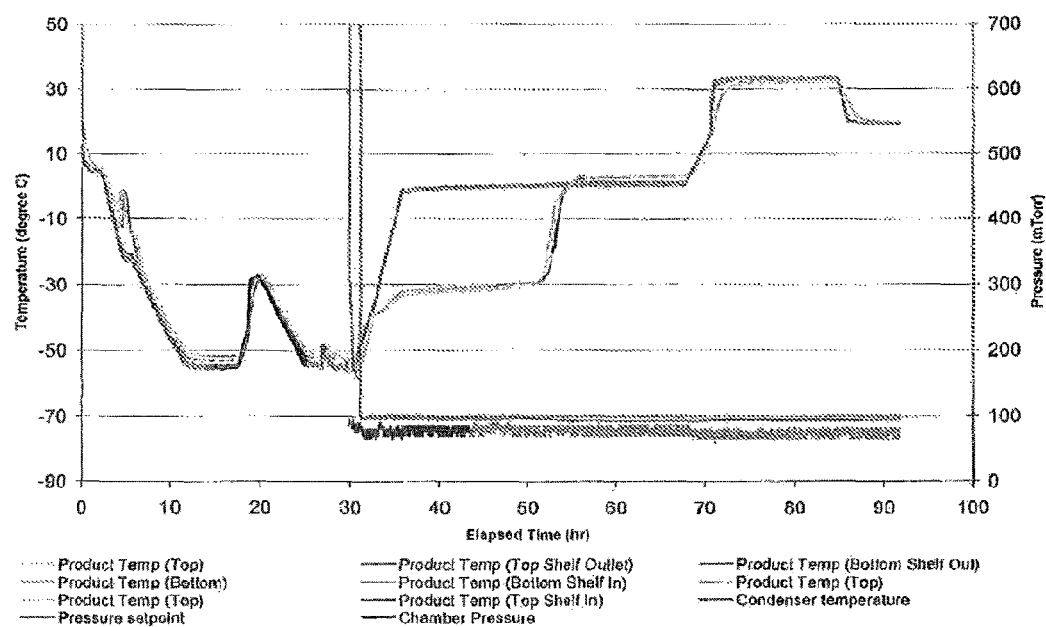
FIG. 17. AT III lyophilization profile when frozen at −60° C. for 6 hrs in Usifroid.
Figure 18:
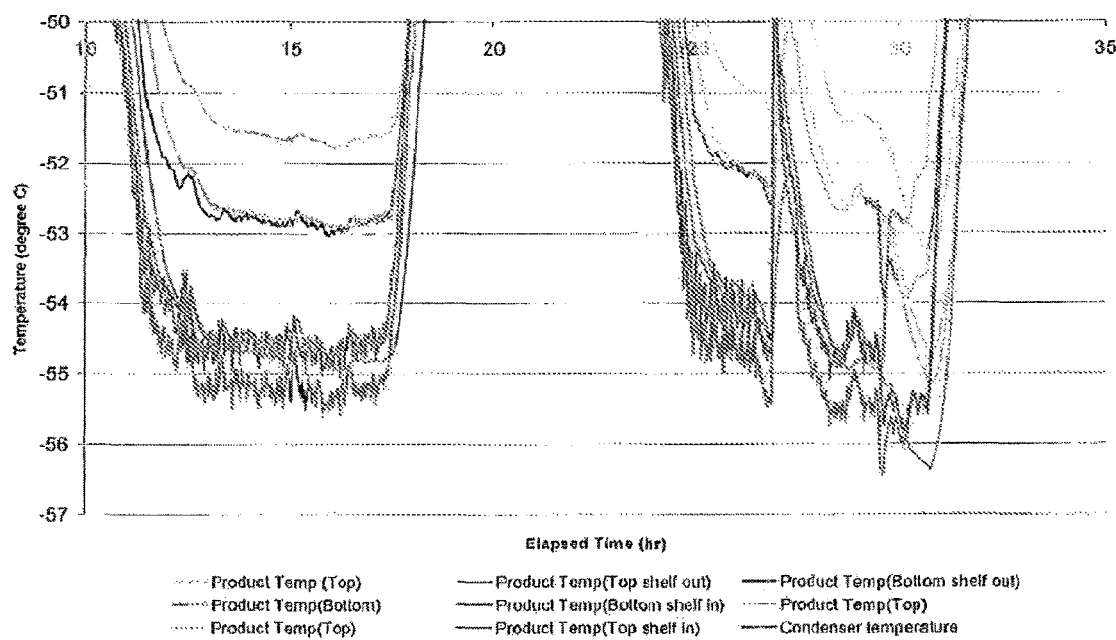
FIG. 18. Product temperature data when ATIII was frozen at −60° C. for 6 hrs in Usifroid.

Freezing at −54° C. for 2 hrs: In this cycle, AT III solution was frozen at −54° C. for 2 hrs, annealed at −30° C. for 1 hr and frozen again at −54° C. for 2 hrs. Freezing was done in the Lyostar II FTS unit. Primary and secondary drying was conducted in the CS 10-0.5 (Serail 14L03). The graphs in FIGS. 11 & 12 showed that the product temperatures were kept below −50° C. during freezing. The physical inspection revealed that 74% cakes were acceptable and 26% had small holes. Even though we see the improvement on the cake appearance by reducing the product temperature from −49° C. to −50° C., the result is still not satisfactory. These results Minilyo freeze dryer (Usifroid). The product temperature was −51.6° C. at the top shelf and −52.7° C. at the bottom shelf during freezing (FIGS. 17 & 18). The physical inspection indicated that all cakes were acceptable. This experiment further demonstrates that decreasing the shelf temperature and extending the freezing hold time are important strategies to produce pharmaceutically acceptable cakes.

Figure 19:
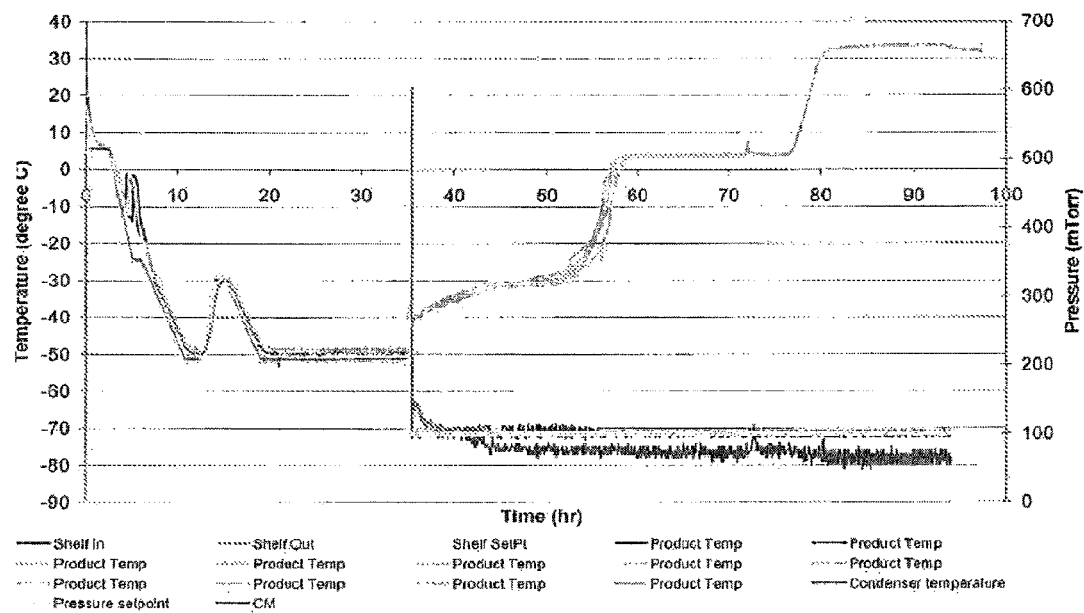
FIG. 19. AT III lyophilization profile when frozen at −52° C. for 15 hrs.
Figure 20:
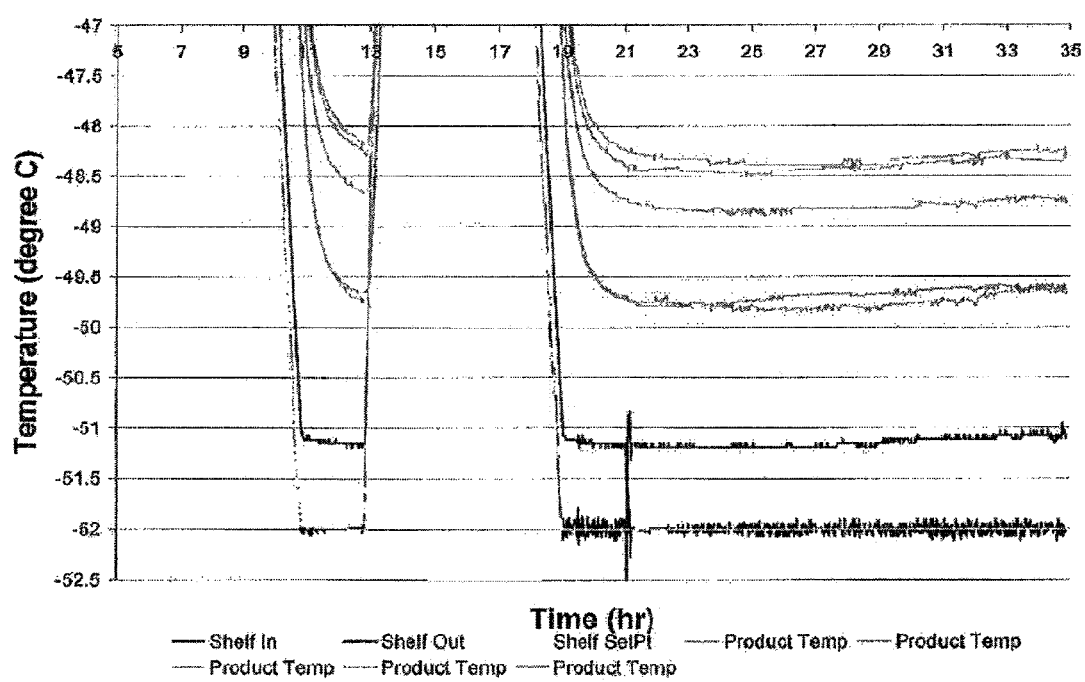
FIG. 20. Product temperature data when frozen at −52° C. for 15 hrs.

Freezing at −52° C. for 15 hrs: In this cycle, AT III solution was frozen at −52° C. for 2 hrs, annealed at −30° C. for 1 hr and frozen again at −52° C. for 15 hrs. Freezing was done in the Lyostar II FTS unit. Primary and secondary drying was conducted in Serail because the isolation valve in FTS got stuck during the primary drying. The warmest product temperatures measured by thermocouples during freezing were below −48° C. (FIGS. 19 & 20). The physical appearance of all cakes was acceptable. Based on the DSC results, −48° C. is the warmest product temperature necessary to induce crystallization. And 15 hr hold time appears to be long enough to ensure complete crystallization.

Summary: Table 4 lists the temperature response to the different shelf temperature set points.

TABLE 4

Temperature response to the different shelf temperature set points.

| Experiment | A | B | C | D | E | F | G | H | I |
|---|---|---|---|---|---|---|---|---|---|
| 1 | FTS | −52 | −52.03 | −51.15 | | | | | −49 |
| 2 | FTS | −54 | −53.99 | −53.15 | −52.46 | −51.75 | −52.38 | −51.98 | −50 |
| 3 | FTS | −54 | −54.03 | −53.23 | −52.19 | −51.81 | −52.24 | −51.77 | −51 |
| 4 | FTS | −50 | −50.07 | −49.18 | −48.59 | −47.46 | −48.51 | −48.12 | −47 |
| 5 | Usifroid | −60 | −58.00 | — | −54.64 | −54.66 | −55.44 | −54.66 | −51.6, −52.7 |
| 4 | FTS | −52 | −51.99 | −51.15 | | | | | 48 |

A = Dryer;
B = Shelf temp Set-pt (° C.);
C = Shelf in (° C.);
D = Shelf out (° C.);
E = Top Shelf in (° C.);
F = Top Shelf out (° C.);
G = Bottom Shelf in (° C.);
H = Bottom Shelf out (° C.); and
I = Product Temp (° C.).

indicate that freezing at low temperature alone is not sufficient to induce complete crystallization.

Figure 13:
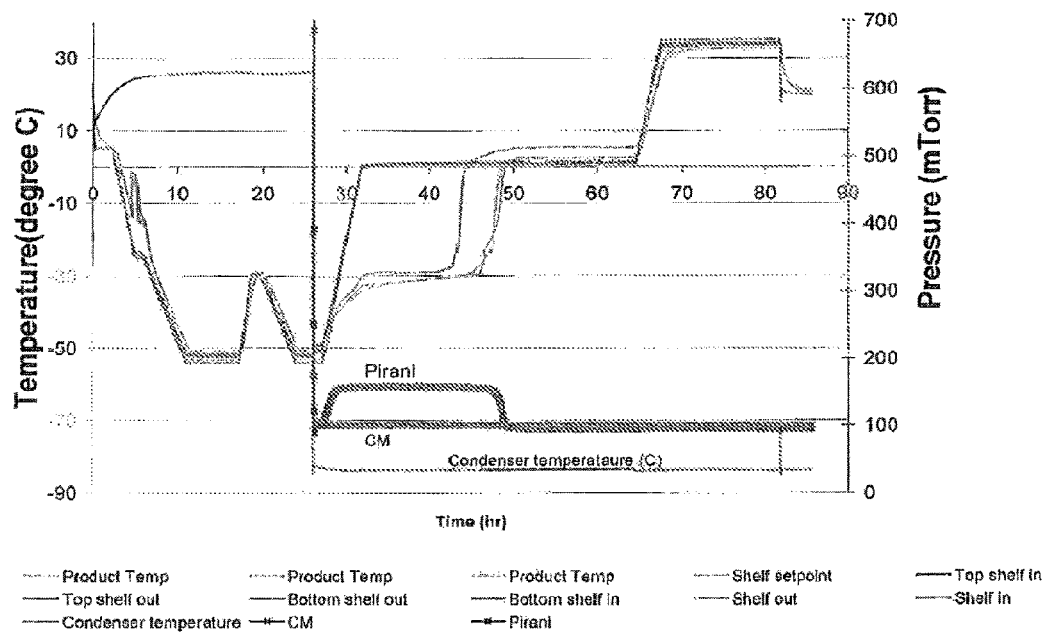
FIG. 13. AT III lyophilization profile when frozen at −54° C. for 6 hrs in FTS unit.
Figure 14:
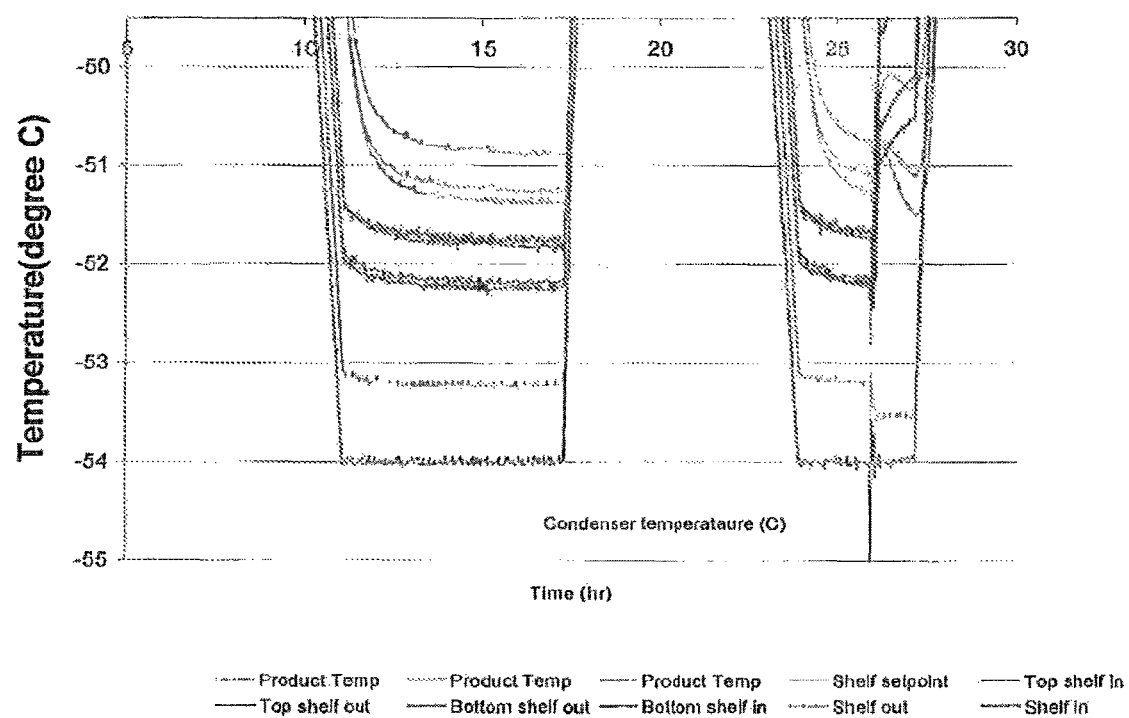
FIG. 14. Product temperature data when frozen at −54° C. for 6 hrs in FTS unit.

Freezing at −54° C. for 6 hrs: In this cycle, AT III solution was frozen at −54° C. for 6 hrs, annealed at −30° C. for 1 hr and frozen again at −54° C. for 2 hrs. The cycle was run in an FTS Freeze-dry unit. The product temperatures were maintained below −50° C. during freezing (FIGS. 13 & 14). The physical inspection indicated that all cakes were acceptable. These results indicate that product temperature and freezing hold time are equally important to ensure optimal crystallization. Such a result is consistent with the DSC observation.

Figure 15:
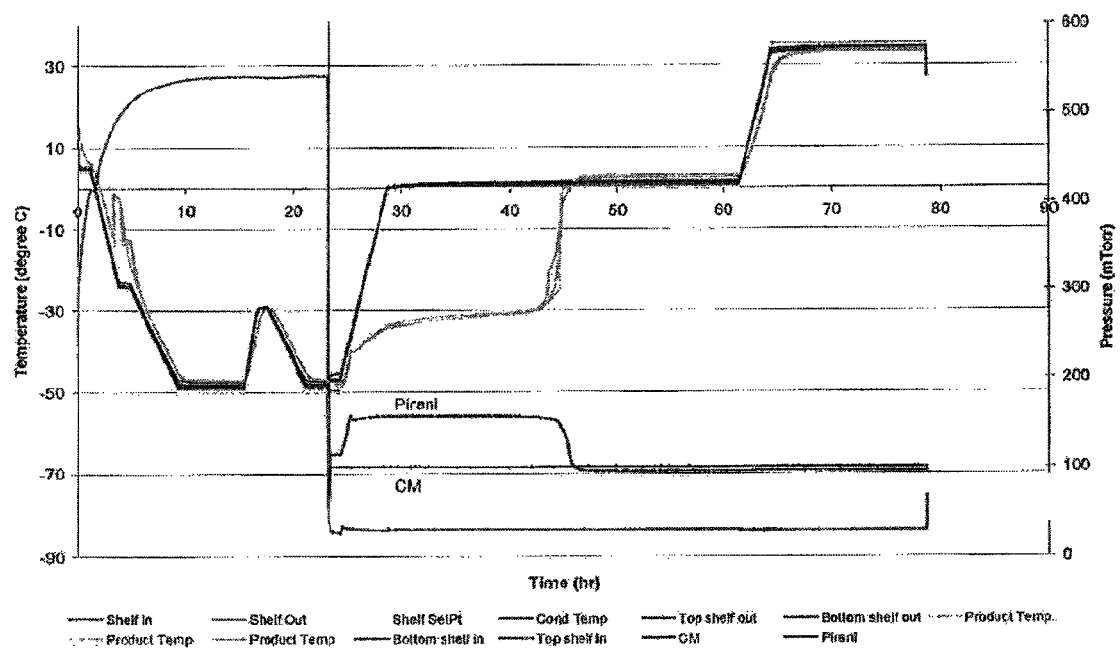
FIG. 15. AT III lyophilization profile when frozen at −50° C. for 6 hrs in FTS unit.
Figure 16:
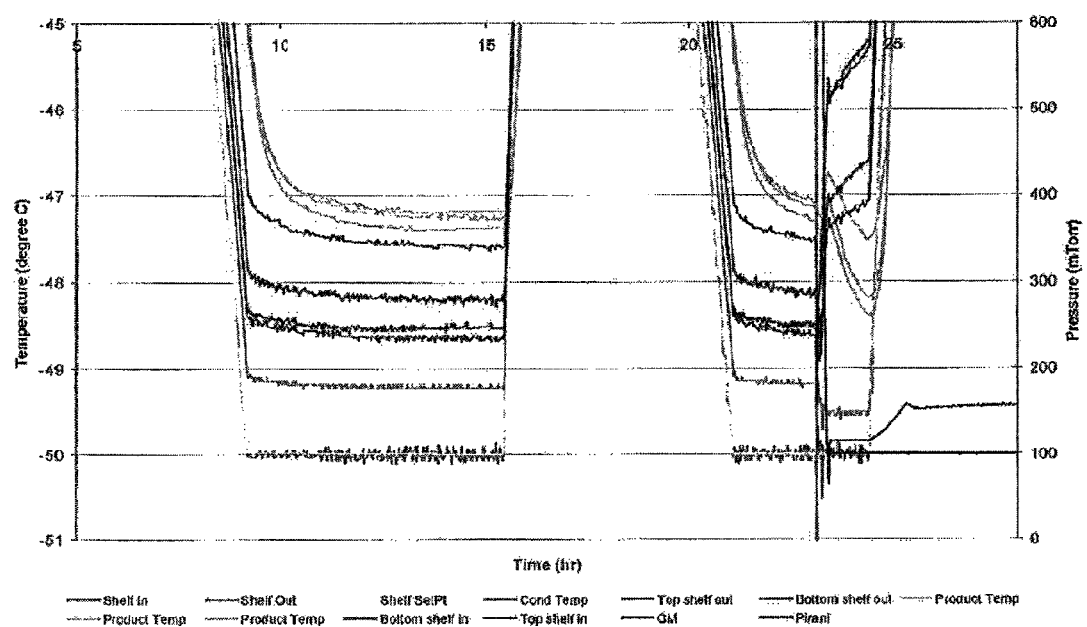
FIG. 16. Product temperature data when frozen at −50° C. for 6 hrs in FTS unit.

Freezing at −50° C. for 6 hrs: In this cycle, AT III solution was frozen at −50° C. for 6 hrs, annealed at −30° C. for 1 hr and frozen again at −50° C. for 2 hrs. The cycle was run in the Lyostar II FTS unit. Using these parameters the product temperatures were maintained below −47° C. and above −48° C. during freezing (FIGS. 15 & 16). The physical inspection indicated that only 18% were acceptable, 23% had small holes and 59% exhibited collapse. This study confirms previous DSC finding that the product temperature needs to be below −48° C. in order to initiate crystallization. It also demonstrates that extension of the freezing hold time alone is not enough to form sufficient crystals.

Freezing at −60° C. for 6 hrs: In this cycle, AT III solution was frozen at −60° C. for 6 hrs, annealed at −30° C. for 1 hr and frozen again at −60° C. for 2 hrs. The cycle was run in the Since the product temperature is typically 4° to 6° C. warmer than the target shelf temperature set point, the target shelf temperature is preferably set at −54° C. to ensure that all product temperatures remain below −48° C. throughout the lyophilizer. Based on the results from these studies (Table 5), the target shelf temperature during freezing can be selected to ensure that the product temperatures are well below −48° C.

TABLE 5

Effect of freezing temperature and hold time on cake appearance.

| | | First | Second | Results | | | |
|---|---|---|---|---|---|---|---|
| No. | Freezing Temp. (° C.) | freezing hold time (hr) | freezing hold time (hr) | A (solid cake) | B* | C** | D*** |
| 1 | −52 | 2 | 2 | 2% | 17% | 57% | 23% |
| 2 | −54 | 2 | 2 | 74% | 26% | — | — |
| 3 | −52 | 2 | 15 | 100% | — | — | — |
| 4 | −50 | 6 | 2 | 18% | 23% | 59% | — |
| 5 | −60 | 6 | 4.5 | 100% | — | — | — |
| 6 | −54 | 6 | 2 | 100% | — | — | — |

*small holes;
**collapsed;
***broken.

In addition, enough time can be allotted to ensure the complete crystallization. The data indicate that a shelf temperature of −54° C. with a 6 hour soak can achieve these conditions and promote adequate crystallization. Therefore, both an extension of the freezing soak time from 2 hrs to 6 hrs and a decrease of target shelf temperature set point from −52 to −54° C. would improve the physical appearance of the finished product.

Figure 21:
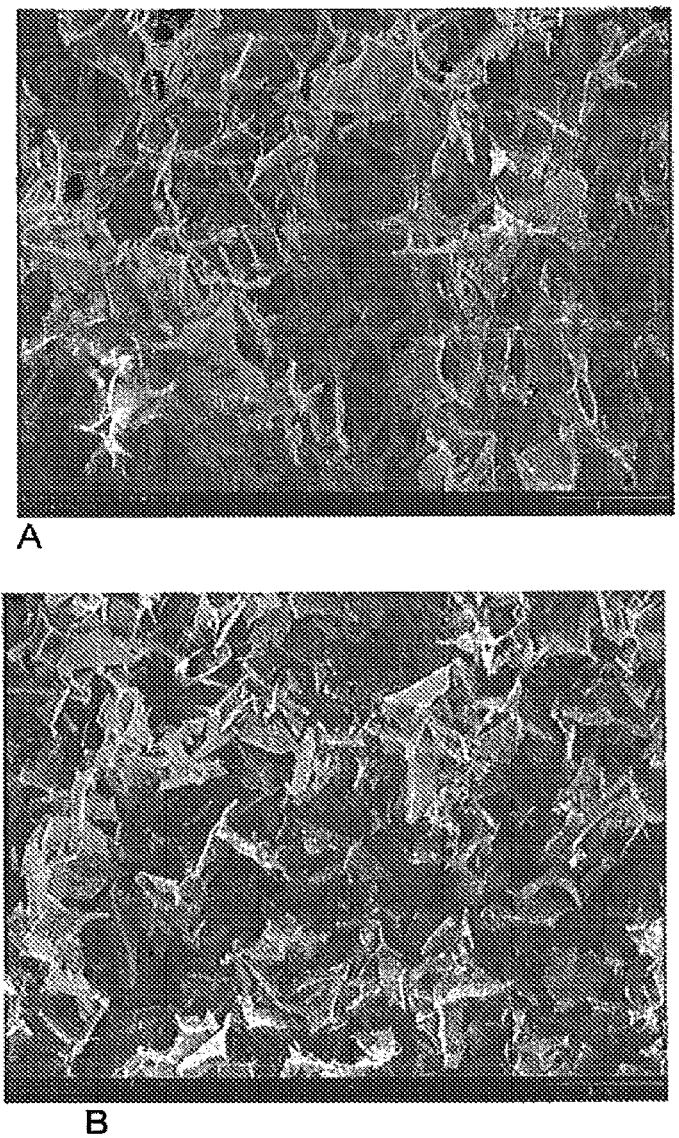
FIG. 21. Scanning electron micrograph of cakes (200× magnification). The scale bars equal to 100 μm. A: a collapsed cake. B: a solid cake.
Figure 22:
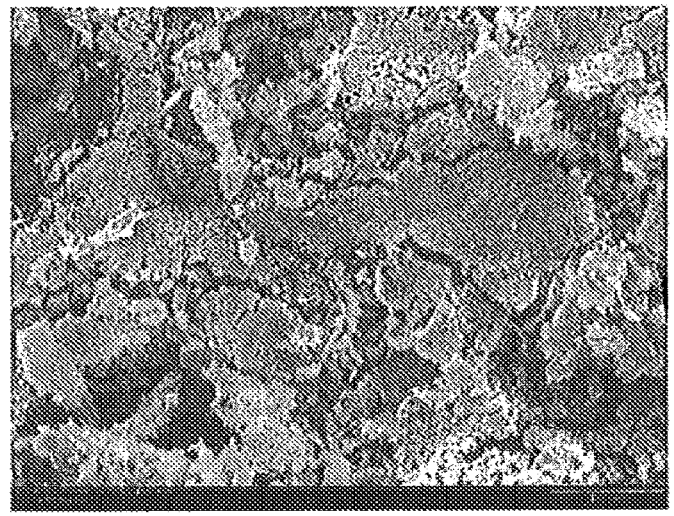
FIG. 22. Scanning electron micrograph of NaCl. 200× magnification on the left and 1500× magnification on the right. The scale bar equals to 100 μm (A) and 10 μm (B).
Figure 22:
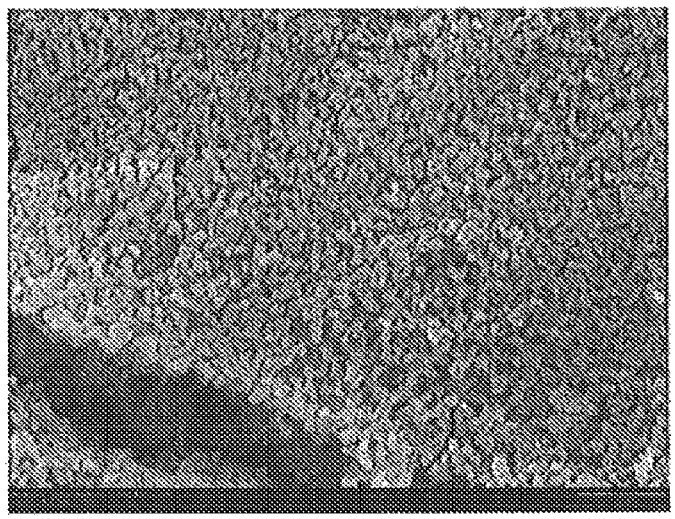
Figure 23:
FIG. 23. Scanning electron micrograph of alanine. 50× magnification on the left and 200× magnification on the right. The scale bar equals to 500 μm (A) and 100 μm (B).
Figure 23:
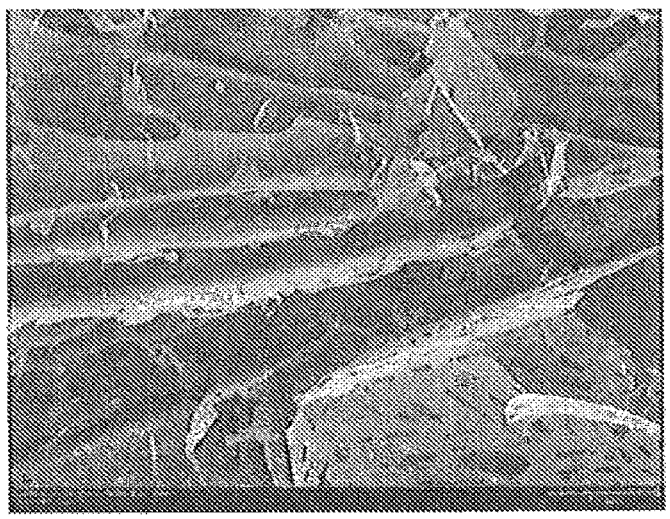

Morphology of freeze-dried cakes: The morphologies of the freeze-dried cakes were observed by a scanning electron microscope. A partially collapsed cake was used as a control for the solid and strong cake. The collapsed cake contains many flakes that are thin and porous (FIG. 21A). A solid cake (FIG. 21B) is mainly composed of plate-shaped crystals with some round crystals distributed throughout the cake. NaCl by itself forms small round crystals (FIG. 22). Alanine alone (FIG. 23) forms continuous plates with some holes probably resulted from ice sublimation. It could be inferred that the plate-shaped crystals in FIG. 21B are primarily from alanine and the round shape crystals from NaCl.

Powder X-ray diffraction: Based on the data generated from the DSC and freezing studies, a second ETP-5807 maximum load run was performed. This run incorporated a lower freezing temperature during the first freezing step as well as extended time to the soak. The modified cycle produced product with acceptable physical appearance.

Figure 24:
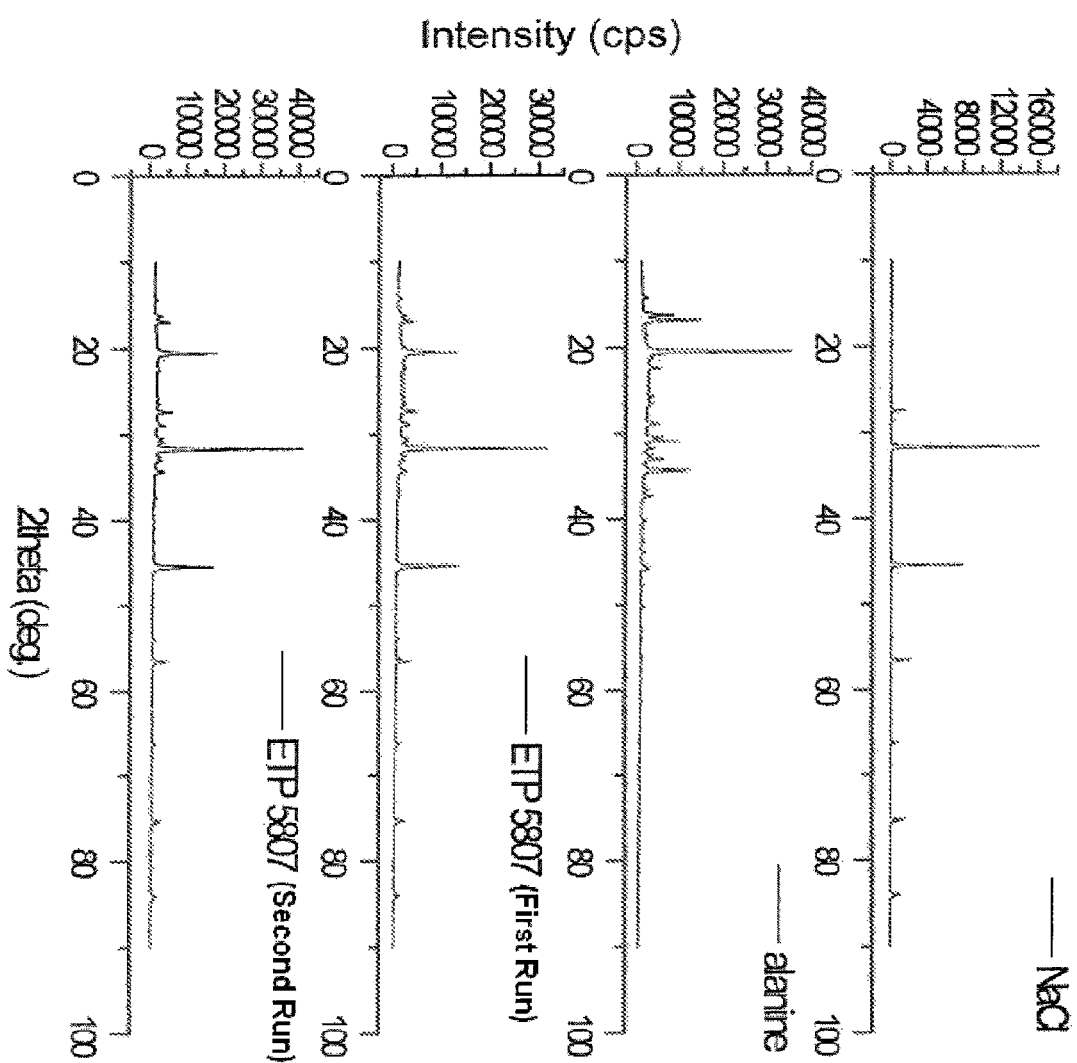
FIG. 24. Powder X-ray diffraction (XRD) patterns using a diffractometer for NaCl, alanine, ETP 5807 (collapsed cake), and material from the second run of ETP 5807 (solid cake).

In order to characterize the crystallinity of a collapsed cake from the first run and a solid cake from the second run, the XRD patterns of NaCl, alanine, ETP 5807 (collapsed cake) and material from the second run of ETP 5807 (solid cake) were evaluated (FIG. 24). The major NaCl crystalline diffraction peaks are at 31.7° and 45.5° 2θ. The main alanine crystalline diffraction peak is at 20.5° 2θ. A broad peak occurring in alanine samples is assigned to the amorphous portion. ETP 5807 ($1^{st}$ run) and ETP 5807 ($2^{nd}$ run) cakes show the peak combination of NaCl and alanine. A broad peak is also observed for both samples.

Crystallinity is calculated by dividing crystalline peak area by the sum of amorphous and crystalline peak area. The crystallinities of NaCl, alanine, ETP 5807 and ETP 5807 ($2^{nd}$ run) are, respectively, fitted to be 99±20%, 50±1%, 66±2% and 60±1%. No difference in the diffraction pattern is noted for the collapsed cake and the solid cake.

Conclusions: The AT III formulation was characterized with emphasis on percent crystallization for the design of the freezing protocol in lyophilization. The results indicate that freezing temperature and hold time are equally important prerequisites for complete crystallization. In some embodiments, lyophilization can comprise a freezing temperature of about −54° C. as well as extended soak time of about 6 hrs. The tests yielded pharmaceutically acceptable finished products.

Example 2

Thirty-ml molded vials were filled with ten milliliters of sterile filtered solution comprising AT III (~6.88 mg/ml), alanine (100 mM (~8.91 mg/ml)), and NaCl (150 mM, (~8.7 mg/ml)). ATIII samples were first frozen to −25° C., held for 2 hrs, and then further frozen to −54° C., followed by holding for 6 hrs. The shelf temperature was then slowly elevated to −30° C. at a rate of 0.2° C./min, and held at that temperature for 2 hrs, and then decreased slowly at 0.2° C./min back to −54° C. The products were held at −54° C. for 2 hrs before starting the primary drying. Primary drying was conducted at a shelf temperature of 0° C. and a controlled chamber pressure of 100 mTorr. Primary drying lasted for approximately 32 hrs before the initiation of secondary drying. The secondary drying was conducted at 35° C. shelf temperature and 100 mTorr chamber pressure for 14 hrs.

Following drying, about 100% pharmaceutically acceptable lyophilized cake resulted. The percentage of pharmaceutically acceptable cake was calculated by dividing the amount of acceptable cake by the number of cakes in the whole batch. Moreover, modulated DSC was applied and the formation of a condensed phase during the freezing stage and the crystallization process during the warming ramp was observed.

We claim:

1. A method of lyophilizing a composition comprising purified antithrombin III (AT III) and one or more crystallizing excipients selected from the group consisting of alanine, mannitol, glycine, and NaCl, the method comprising:
   (a) exposing the composition to a temperature range of between −48 to −54° C.;
   (b) maintaining the temperature of the composition between −48 to −54° C. for a period of about 4 to 10 hours prior to lyophilization.

2. The method of claim 1, wherein the first period of time is at least about 5 hours.

3. The method of claim 1, wherein the crystallizing excipients are alanine and NaCl.

4. The method of claim 3, wherein the alanine and the NaCl are present in the composition at about 100 mM each.

5. The method of claim 1, wherein the first temperature and the first period of time are sufficient such that the at least one crystallizing excipient is completely or nearly completely crystallized.

6. The method of claim 1, wherein the composition further comprises one or more excipients each selected from the group consisting of: a stabilizing agent, a buffering agent, a surfactant, an antioxidant, and a divalent cation.

7. The method of claim 1, wherein the composition further comprises a buffer selected from the group consisting of: phosphate buffer, acetate buffer, citrate buffer, and citric acid/phosphate buffer, histidine, tris-(hydroxymethyl)-aminomethane, 1,3-bis-[tris-(hydroxy-methyl)methylamino]-propane, histidine, piperazine-N,N'-bis-(2-ethanesulfonic acid), 3-(N-morpholino) propanesulfonic acid, N-2-hydroxyethyl-piperazine-N'-2-ethanesulfonic acid, 2-(N-morpholino) ethanesulfonic acid and N-2-acetamido-2-aminoethanesulfonic acid.

8. The method of claim 1, further comprising drying the first composition to obtain a lyophilized cake.

9. The method of claim 1, wherein the lyophilized cake is at least 50% solid cake.

10. The method of claim 1, wherein the composition is a liquid pharmaceutical composition comprising a pharmaceutically acceptable carrier.

11. The method of claim 1, further comprising exposing the first composition to a second temperature for a second period of time to obtain a second composition, wherein the second temperature is higher than the first temperature.

12. The method of claim 11, further comprising exposing the second composition to a third temperature for a third period of time to obtain a third composition, wherein the third temperature is lower than the second temperature.

13. The method of claim 12, further comprising drying the third composition to obtain a lyophilized cake.

14. A kit comprising the lyophilized cake of claim 8.

15. A method of lyophilizing a liquid composition comprising purified, plasma-derived antithrombin III (AT III), NaCl, and alanine, the method comprising:
   (a) exposing the composition to about −54° C. or below such that the temperature of the composition is about −48° C. or below for at least about 5 hours or more in order to provide a first composition having one or more components therein completely or near completely crystallized; and (b) drying the first composition to obtain a lyophilized cake.

16. The method of claim 15, wherein the potency of the AT III is maintained following storage of the lyophilized cake at about 25° C. to about 40° C. for about 1 to about 6 months.

17. The method of claim 15, wherein the alanine and the NaCl are present in the composition at about 100 mM each.

18. The method of claim 15, wherein the composition further comprises one or more excipients each selected from the group consisting of: a stabilizing agent, a buffering agent, a surfactant, an antioxidant, and a divalent cation.

* * * * *